US010507211B2

(12) United States Patent
Li et al.

(10) Patent No.: US 10,507,211 B2
(45) Date of Patent: Dec. 17, 2019

(54) TREATMENT FOR HEREDITARY NEUROPATHY WITH LIABILITY TO PRESSURE PALSIES (HNPP)

(71) Applicants: Vanderbilt University, Nashville, TN (US); The United States Government as represented by the Department of Veterans Affairs, Washington, DC (US)

(72) Inventors: Jun Li, Brentwood, TN (US); Bo Hu, Brentwood, TN (US)

(73) Assignees: Vanderbilt University, Nashville, TN (US); The United States as represented by the Department of Veterans Affairs, Washington, DC (US)

( * ) Notice: Subject to any disclaimer, the term of this patent is extended or adjusted under 35 U.S.C. 154(b) by 0 days.

(21) Appl. No.: 15/651,931

(22) Filed: Jul. 17, 2017

(65) Prior Publication Data

US 2018/0036311 A1 Feb. 8, 2018

Related U.S. Application Data

(60) Provisional application No. 62/363,044, filed on Jul. 15, 2016.

(51) Int. Cl.
*A61K 31/519* (2006.01)

(52) U.S. Cl.
CPC .................. *A61K 31/519* (2013.01)

(58) Field of Classification Search
None
See application file for complete search history.

(56) References Cited

U.S. PATENT DOCUMENTS

| 2013/0084275 A1* | 4/2013 | Bokel | A61K 38/45 424/94.5 |
| 2014/0107222 A1* | 4/2014 | Shekhar | A61K 31/105 514/707 |

OTHER PUBLICATIONS

Etemadifar et al., Multiple sclerosis and neurofibromatosis type 1: report of seven patients from Iran, Mult Scler. Sep. 2009;15(9): 1126-30, printed from https://www.ncbi.nlm.nih.gov/pubmed/19692435, 1 page, Abstract only (Year: 2009).*
Winfield, Pharmaceutical Practice, Oral unit dosage forms, Churchill Livingstone, fourth edition, 2009, 393-398 (Year: 2009).*
Link et al., Increased transforming growth factor-beta, interleukin-4, and interferon-gamma in multiple sclerosis, Ann Neurol. Sep. 1994;36(3):379-386, printed from https://www.ncbi.nlm.nih.gov/pubmed/8080246, 1 page, abstract only (Year: 1994).*
National Multiple Sclerosis Society, MS Symptoms, Mar. 13, 2014, printed from https://web.archive.org/web/20140313094038/https://www.nationalmssociety.org/Symptoms-Diagnosis/MS-Symptoms, 5 pages (Year: 2014).*
Guo, et al., Abnormal junctions and permeability of myelin in PMP22-deficient nerves. Ann Neurol. 2014;75(2):255-65. Epub Dec. 18, 2013. doi: 10.1002/ana.24086. PubMed PMID: 24339129; PubMed Central PMCID: PMC4206215.
Hu, et al., Tuning PAK Activity to Rescue Abnormal Myelin Permeability in HNPP; PLOS Genetics | DOI:10.1371/journal.pgen.1006290 Sep. 1, 2016; pp. 1-24.

* cited by examiner

*Primary Examiner* — Gigi G Huang
(74) *Attorney, Agent, or Firm* — Stites & Harbison PLLC; Mandy Wilson Decker

(57) ABSTRACT

A method of treating demyelinating diseases involves administering a PAK1 inhibitor that is PF-3758309 to a subject in need of such treatment.

14 Claims, 10 Drawing Sheets

Specification includes a Sequence Listing.

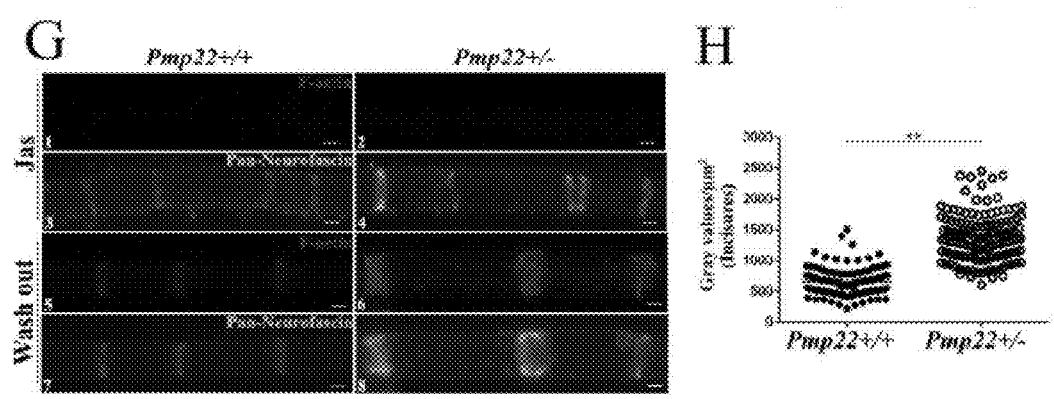
FIG. 4, cont'd

SEQUENCE LISTING

```
<160> NUMBER OF SEQ ID NOS: 4

<210> SEQ ID NO 1
<211> LENGTH: 33
<212> TYPE: DNA
<213> ORGANISM: Artificial Sequence
<220> FEATURE:
<223> OTHER INFORMATION: Engineered Primer

<400> SEQUENCE: 1
```

```
                                        -continued cccaagcttg ccaccatggg cccttggagc cgc                                    33

<210> SEQ ID NO 2
<211> LENGTH: 33
<212> TYPE: DNA
<213> ORGANISM: Artificial Sequence
<220> FEATURE:
<223> OTHER INFORMATION: Engineered Primer

<400> SEQUENCE: 2
ccgctcgaga aacagcaaga gcagcagaat cag                                    33

<210> SEQ ID NO 3
<211> LENGTH: 38
<212> TYPE: DNA
<213> ORGANISM: Artificial Sequence
<220> FEATURE:
<223> OTHER INFORMATION: Engineered Primer

<400> SEQUENCE: 3
cggggtaccg ccaccatgat tctggggatt cttggagg                               38

<210> SEQ ID NO 4
<211> LENGTH: 25
<212> TYPE: DNA
<213> ORGANISM: Artificial Sequence
<220> FEATURE:
<223> OTHER INFORMATION: Engineered Primer

<400> SEQUENCE: 4
ccgctcgagg tcgtcctcgc cgcct                                             25
```

TREATMENT FOR HEREDITARY NEUROPATHY WITH LIABILITY TO PRESSURE PALSIES (HNPP)

RELATED APPLICATIONS

This application claims priority from U.S. Provisional Application Ser. No. 62/363,044, filed Jul. 15, 2016, the entire disclosure of which is incorporated herein by this reference.

GOVERNMENT INTEREST

This invention was made with government support under grant number R01NS066927 awarded by the National Institutes of Health. The government has certain rights in the invention.

TECHNICAL FIELD

The presently-disclosed subject matter generally relates to treatment of hereditary neuropathy with liability to pressure palsies (HNPP) and other demyelinating diseases. In particular, certain embodiments of the presently-disclosed subject matter relate to treatment of HNPP using a PAK1 inhibitor.

INTRODUCTION

Myelin prevents the outward-current from shunting and preserves depolarizing current for the induction of action potentials at the nodes of Ranvier. This current is five times higher than the minimum required to trigger the action potential. This surplus is called the "safety factor" [1]. Although demyelination is widely regarded as one of the most important mechanisms altering the safety factor, effective nerve conduction is also thought to require a proper myelin seal through myelin junctions such as tight junctions and adherens junctions. These junctions seal the spaces between adjacent myelin lamellae and between the myelin and axolemma [2].

Excessively permeable myelin (i.e., an increase of capacitance) has been observed in a mouse model of hereditary neuropathy with liability to pressure palsies (HNPP) due to disruption of these myelin junctions. As used herein, this unique mechanism is referred to as "functional demyelination." With reference to Panel A of FIG. 1, this mechanism impairs action potential propagation in the absence of demyelination [3]. Thus, this mechanism denotes pathological processes that may alter the insulating quality of myelin without physically stripping off the myelin sheath.

HNPP is caused by a heterozygous deletion of PMP22 gene in human chromosome 17p12. PMP22 encodes a tetra-span membrane protein primarily expressed in peripheral nerve myelin [4-6]. Mice with heterozygous knockout of Pmp22 recapitulate the pathology of humans with HNPP, including tomacula with excessive myelin decompaction that extends from paranodes to juxtaparanodes and internodes [7]. Application of mechanical compression on Pmp22+/− mouse nerves induced conduction block (i.e., failure of action potential propagation) more rapidly than that in Pmp22+/+ nerves. This finding is consistent with the key clinical features in patients with HNPP—focal sensory loss and weakness when nerves are exposed to mild mechanical stress [8, 9]. Therefore, these mice have become an authentic model of HNPP.

There are three types of junctions in myelin: tight junctions, adherens junctions, and septate junctions [2]. With reference to Panel A of FIG. 1, all are mainly in non-compact myelin regions: paranodal loops, Schmidt-Lanterman incisures (SLI), and inner/outer mesaxons [10]. With reference to Panel B of FIG. 1, although each type of junctions has distinct protein constituents, they share similar molecular architectures. For instance, tight junctions are formed by polymerization of claudins, a family of tetraspan membrane proteins. C-terminals of claudins interact with a group of cytoplasmic adaptors such as ZO1 or ZO2 [11]. These PDZ-containing proteins directly interact with actins and link the tight junctions to the cytoskeleton for stabilization [12]. Adherens junctions employ a similar organization. E-cadherin has a glycosylated extracellular domain, a single transmembrane domain, and a cytoplasmic c-terminal tail that interacts with adaptor catenins ($\alpha$-catenin, $\beta$-catenin and p120 catenin). $\alpha$-catenin directly interacts with actin filaments. The actin network is subject to the regulation of small GTPases (Cdc42 or Rac1) and their effectors such as p21-activated kinase (PAK1) [12].

Furthermore, all junctions are strengthened by a group of Ig-domain proteins, such as JAM-C in myelin, that form transmembrane dimers juxtaposed to the junctions to seal the space between the opposing membranes [13]. Because actin networks are involved in the stabilization of all junctions, it is contemplated herein that PMP22 deficiency disrupts myelin junctions by altering actin polymerization.

HNPP is known as a demyelinating disease. Examples of demyelinating diseases additionally include multiple sclerosis (MS), optic neuritis, neuromyelitis optica, also known as Devic's disease (NMO), transverse myelitis (TM), acute disseminated encephalomyelitis, adrenoleukodystrophy and adrenomyeloneuropathy, Tabes dorsalis (syphilitic myelopathy), leukoencephalopathies, Progressive multifocal leukoencephalopathy, leukodystrophies, Guillain-Barré syndrome, chronic inflammatory demyelinating polyneuropathy, anti-MAG peripheral neuropathy, Charcot-Marie-Tooth disease—type I, Leber's Hereditary Optic Neuropathy, copper deficiency associated conditions, and progressive inflammatory neuropathy.

Symptoms associated with demyelinating diseases vary among individuals and/or specific conditions, but examples include, numbness, loss of reflexes and uncoordinated movements, poorly controlled blood pressure, blurred vision, dizziness, racing heart beat or palpitations, memory problems, pain, loss of bladder and bowel control, fatigue, numbness, tingling, loss of muscle function (palsy), and pain. Demyelinating diseases impact millions of people and their inception and progression can be devastating. There are not currently any cures for demyelinating diseases, and treatment options are limited. Accordingly, there is a need in the art for treatments for demyelinating diseases

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter includes methods and compositions for use in treating demyelinating diseases. Methods of the presently-disclosed subject matter involve administering a selective PAK1 inhibitor that is PF-3758309 to a subject in need of treatment for a demyelinating disease. PF-3758309 is a compound having the following structure:

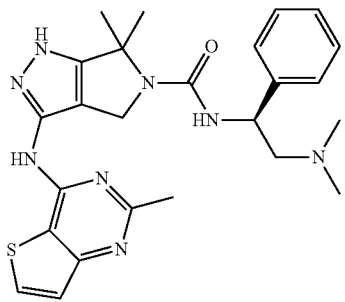 [SMILES: Cc1nc(Nc2n[nH]c3c2CN(C(=O)N[C@H](CN(C)C)c2ccccc2)C3(C)C)c2sccc2n1]

Hereditary neuropathy with liability to pressure palsies (HNPP), for example, is a demyelinating disease that is an inherited peripheral nerve disease. Other examples of demyelinating diseases include multiple sclerosis (MS), optic neuritis, neuromyelitis optica, also known as Devic's disease (NMO), transverse myelitis (TM), acute disseminated encephalomyelitis, adrenoleukodystrophy and adrenomyeloneuropathy, some myelopathies, Tabes dorsalis (syphilitic myelopathy), leukoencephalopathies, Progressive multifocal leukoencephalopathy, leukodystrophies, Guillain-Barré syndrome, chronic inflammatory demyelinating polyneuropathy, anti-MAG peripheral neuropathy, Charcot-Marie-Tooth disease—type I, Leber's Hereditary Optic Neuropathy, copper deficiency associated conditions, and progressive inflammatory neuropathy. Additional demyelinating diseases can be found at the following archived site: web.archive.org/web/20170717155146/http://www.merckmanuals.com/professional/neurologic-disorders/demyelinating-disorders/overview-of-demyelinating-disorders.

DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

DESCRIPTION OF EXEMPLARY EMBODIMENTS

Figure 1:
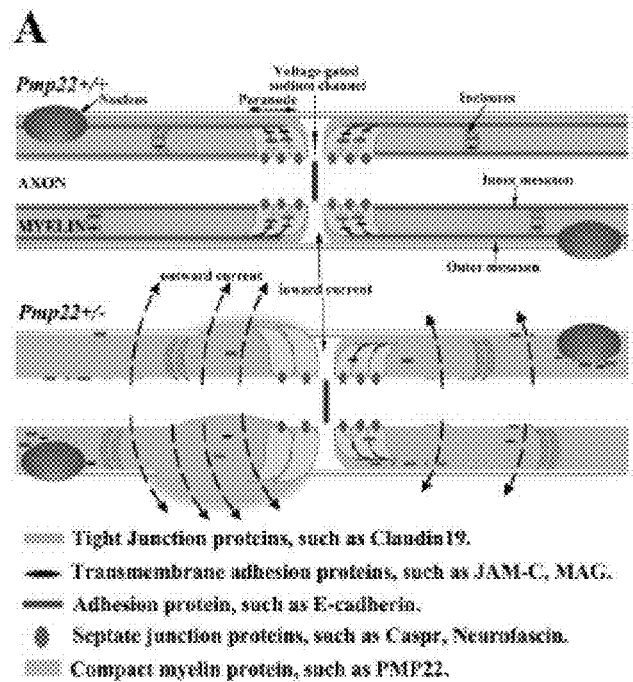
FIG. 1. includes a schematic illustration of myelin disruption. Panel A of FIG. 1 illustrates the mechanism of functional demyelination (modified from Guo et al Ann Neurol 2014). Myelin junctions in Pmp22+/+ nerve are in non-compact myelin regions, including paranodes, incisures and mesaxons. These junctions seal the spaces between myelin lamina. A Pmp22+/− nerve fiber is depicted and develops a tomaculae in the left paranode extending into juxtaparanode and internode, but there is no segmental demyelination. However, junction protein complexes are disrupted or disappeared in the non-compact myelin. These junction proteins may be found in aberrant locations, including perinuclear areas or tomaculous myelin. Abnormal junctions in Pmp22+/− nerves increase myelin permeability (or increase of capacitance). Panel B of FIG. 1 illustrates the molecular architecture of junction protein complex, wherein transmembrane proteins establish "trans-adhesion" between opposing membranes. Through adaptor proteins, such as ZO1/2 or catenins, these junction protein complexes are stabilized by sub-membrane actin networks. Alteration of the actin network has been shown to disassemble junctions in epithelial cell models [27, 28].
Figure 1:
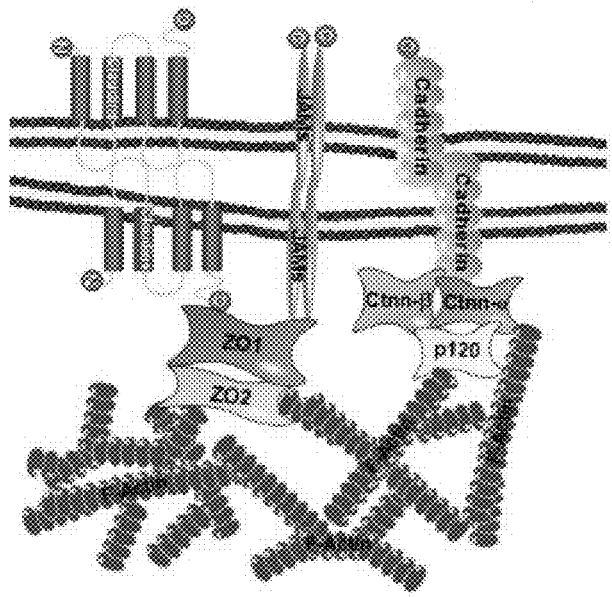

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter includes methods and compositions for use in treating demyelinating diseases. Methods of the presently-disclosed subject matter involve administering an effective amount of a selective PAK1 inhibitor. In some embodiments, the methods involve administering an effective amount of PF-3758309 to a subject in need of treatment for a demyelinating disease. PF-3758309 is a compound having the following structure:

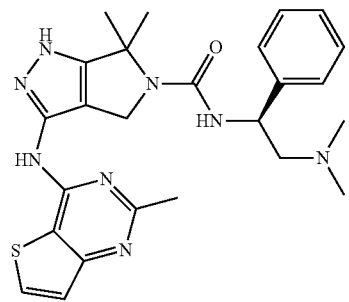 [SMILES: Cc1nc(Nc2n[nH]c3c2CN(C(=O)N[C@H](CN(C)C)c2ccccc2)C3(C)C)c2sccc2n1]

Hereditary neuropathy with liability to pressure palsies (HNPP), for example, is a demyelinating disease that is an inherited peripheral nerve disease. Other examples of demyelinating diseases include multiple sclerosis (MS), optic neuritis, neuromyelitis optica, also known as Devic's disease (NMO), transverse myelitis (TM), acute disseminated encephalomyelitis, adrenoleukodystrophy and adrenomyeloneuropathy, some myelopathies, Tabes dorsalis (syphilitic myelopathy), leukoencephalopathies, Progressive multifocal leukoencephalopathy, leukodystrophies, Guillain-Barré syndrome, chronic inflammatory demyelinating polyneuropathy, anti-MAG peripheral neuropathy, Charcot-Marie-Tooth disease—type I, Leber's Hereditary Optic Neuropathy, copper deficiency associated conditions, and progressive inflammatory neuropathy. Additional demyelinating diseases can be found at the following archived site from Jul. 17, 2017: web. archive. org/web/20170717155146/http://www.merckmanuals.com/professional/neurologic-disorders/demyelinating-disorders/overview-of-demyelinating-disorders.

The presently-disclosed subject matter is based, in part, on the unexpected discoveries highlighted in the studies described herein. Briefly, disruption of myelin junctions, such as tight junctions and adherens junctions, are found in an animal model of hereditary neuropathy with liability to pressure palsies (HNPP). A robust increase of F-actin was observed in nerve regions where myelin junctions were disrupted, leading to increased myelin permeability. The presence of excessively-permeable myelin due to disruption of these myelin junctions is referred to herein as "functional demyelination." These abnormalities were present long before segmental demyelination. Therefore, functional demyelination represents an upstream mechanism prior to the actual stripping of myelin, a key pathology shared by many demyelinating diseases.

Furthermore, the increase of F-actin levels correlated with an enhanced activity of p21-activated kinase (PAK1), a molecule known to regulate actin polymerization. Pharmacological inhibition of PAK1 normalized levels of F-actin, and completely prevented the progression of the myelin junction disruption and nerve conduction failure in the animal model. In particular, administration of the PAK1 inhibitor, PF-3758309, achieved these results; however, not every PAK1 inhibitor will work.

Indeed, two additional PAK inhibitors, FRAX597 and FRAX486, were tested, but they failed to inhibit PAK1 activity in the animal peripheral nerves and were not suitable for the treatment.

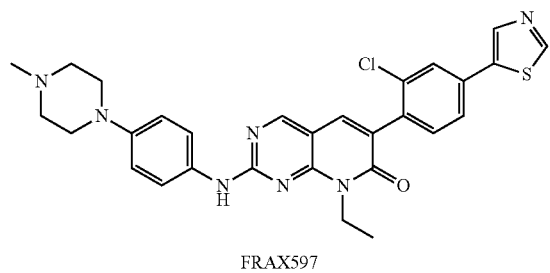

FRAX597

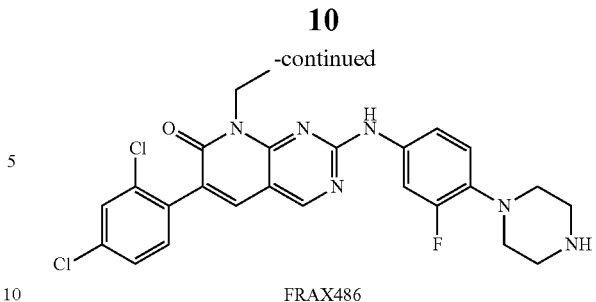

FRAX486

Without wishing to be bound by theory or mechanism, it is contemplated that this failure was due to poor penetrance of the compounds into the peripheral nerve system. Meanwhile, PF-3758309 appears to have the ability to penetrate into the peripheral nerve system, which is unexpected. In fact, PF-3758309 was previously known for its anticancer activity [22, 23]. It is also noted that the effective dose of PF-3758309 when used for treatment in a skin cancer animal model [22] was 100 times higher than the effective dose of PF-3758309 used in the studies described herein related to treatment of demyelinating diseases.

Conventional methods of extrapolating human dosage based on doses administered to a murine animal model can be carried out using the conversion factor for converting the mouse dosage to human dosage: Dose Human per kg=Dose Mouse per kg×12 (Freireich et al., (1966) Cancer Chemother Rep. 50:219-244). Drug doses can also be given in milligrams per square meter of body surface area. Body surface area can be used as a common denominator for drug dosage in adults and children as well as in different animal species as described by Freireich et al. (Freireich et al., (1966) Cancer Chemother Rep. 50:219-244). Briefly, to express a mg/kg dose in any given species as the equivalent mg/sq m dose, multiply the dose by the appropriate km factor. In an adult human, 100 mg/kg is equivalent to 100 mg/kg×37 kg/sq m=3700 mg/m$^2$.

The presently-disclosed subject matter includes a method of treating a demyelinating disease, which includes administering to a subject in need thereof an effective amount of a PAK1 inhibitor that is PF-3758309.

A "demyelinating disease" is a disease that results in damage to the protective covering, or myelin sheath, that surrounds nerve fibers in the brain, optic nerves, and/or spinal cord of a subject. Examples of demyelinating diseases include hereditary neuropathy with liability to pressure palsies (HNPP), multiple sclerosis (MS), optic neuritis, neuromyelitis optica, also known as Devic's disease (NMO), transverse myelitis (TM), acute disseminated encephalomyelitis, adrenoleukodystrophy and adrenomyeloneuropathy, some myelopathies, Tabes dorsalis (syphilitic myelopathy), leukoencephalopathies, Progressive multifocal leukoencephalopathy, leukodystrophies, Guillain-Barré syndrome, chronic inflammatory demyelinating polyneuropathy, anti-MAG peripheral neuropathy, Charcot-Marie-Tooth disease—type I, Leber's Hereditary Optic Neuropathy, copper deficiency associated conditions, and progressive inflammatory neuropathy. As used herein, "demyelinating disease" is inclusive of "functional demyelination," a condition including presence of excessively-permeable myelin due to disruption of myelin junctions, which occurs prior to the actual stripping of myelin. As used herein, "demyelinating disease" is inclusive of a condition in which myelin sheath has been damaged or stripped.

As used herein "treatment" and "treating" refer to prophylactic treatment and therapeutic treatment. As such, the terms treatment or treating include, but are not limited to: (i) preventing, reducing, delaying, or arresting progression of: a demyelinating disease; myelin junction disruption and nerve conduction failure; myelin permeability; and/or damage or stripping of myelin; (ii) causing a regression a demyelinating disease; myelin junction disruption and nerve conduction failure; myelin permeability; and/or damage or stripping of myelinin; and/or (ii) ameliorating or relieving symptoms associated with a demyelinating disease. Examples of symptoms associated with a demyelinating disease include numbness, a sensation of "pins and needles," loss of reflexes and uncoordinated movements, poorly controlled blood pressure, blurred vision, memory problems, pain, loss of bladder and bowel control, fatigue, numbness, tingling, loss of muscle function (palsy), and pain.

In some embodiments, the treatment method of the presently-disclosed subject matter further includes the step of monitoring the subject's symptoms that are associated with demyelinating diseases. In some embodiments, the method further includes the step of monitoring one or more symptoms selected from the group consisting of numbness, loss of reflexes and uncoordinated movements, poorly controlled blood pressure, blurred vision, memory problems, pain, loss of bladder and bowel control, fatigue, numbness, tingling, loss of muscle function (palsy), and pain.

The terms "subject" or "subject in need thereof" refer to a target of administration, which optionally displays symptoms related to a demyelinating disease. The subject can be a mammal, such as a human, non-human primate, horse, pig, rabbit, dog, sheep, goat, cow, cat, guinea pig or rodent. The term does not denote a particular age or sex.

In some embodiments of the method disclosed herein, the subject is a mammal. In some embodiments, the subject is a human. In some embodiments, the method further includes a step of selecting a subject who has been identified has having functional demyelination or a risk thereof. In some embodiments, the method further includes a step of selecting a subject who has been identified has having a demyelinating disease or a risk thereof. As will be understood, assessing risk of having or developing a condition and/or making a diagnosis refer to methods by which the skilled artisan, e.g., a physician, can estimate and even determine whether or not a subject is suffering from a given disease or condition. The skilled artisan often makes an assessment based on a physical examination and/or on the basis of one or more diagnostic indicators.

As used herein, the terms "effective amount" refers to a dosage sufficient to provide treatment. The exact amount that is required will vary from subject to subject, depending on the species, age, and general condition of the subject, the particular carrier or adjuvant being used, mode of administration, and the like. As such, the effective amount will vary based on the particular circumstances, and an appropriate effective amount can be determined in a particular case by one of ordinary skill in the art using only routine experimentation.

In some embodiments of the presently-disclosed method, the effective dose of PF-3758309 is significantly reduced relative to use of the compound for treatment of skin cancer. In some embodiments of the presently-disclosed method, the PAK1 inhibitor is administered at a dose at least about 15, 20, 25, 30, 35, 40, 45, 50, 55, 60, 65, 70, 75, 80, 85, 90, 95, 100, 105, 110, 115, 120, 125, 130, 135, 140, 145, or 150 times lower than a dose used for cancer treatment. In some embodiments, the dose used for skin cancer treatment is about 15-300 mg/kg. In some embodiments, the dose used for skin cancer treatment is about 25-250 mg/kg. In some embodiments, the dose used for skin cancer treatment is about 25, 50, 75, 100, 125, 150, 200, 225, 250, or 300 mg/kg. In some embodiments, the dose used for skin cancer treatment is about 25 mg/kg.

In some embodiments of the presently-disclosed method, the PAK1 inhibitor is administered at a dose of about 0.03 to about 0.05, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.05, 1.1, 1.15, 1.2, 1.25, 1.3, 1.35, 1.4, 1.45, 1.5, 1.55, 1.6, 1.65, 1.7, 1.75, 1.8, 1.85, 1.9, 2, 2.05, 2.1, 2.15, 2.2, 2.25, 2.3, 2.35, 2.4, 2.45, 2.5, 2.55, 2.6, 2.65, 2.7, 2.75, 2.8, 2.85, 2.9, 2.95, or 3 mg/kg. In some embodiments, the PAK1 inhibitor is administered at a dose of about 0.25-3 mg/kg. In some embodiments, the PAK1 inhibitor is administered at a dose of about 0.03-3 mg/kg. In some embodiments, the PAK1 inhibitor is administered at a dose of about 0.03-1 mg/kg.

In other embodiments, the PAK1 inhibitor is administered at a dose of about 1-30 mg/kg. In some embodiments, the PAK inhibitor is administered at a dose up to about 100 mg/kg.

In some embodiments of the presently-disclosed method, the PAK1 inhibitor is provided in a composition, which includes PF-3758309 and a pharmaceutically acceptable carrier. As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. In some embodiments, the PAK1 inhibitor is provided in a composition together with a second active ingredient, such as a known treatment agent for a demyelinating disease or symptom thereof.

In some embodiments of the presently-disclosed method, the PAK1 inhibitor-containing composition is provided in a unit dose form. As used herein, a "unit dose form" refers to physically discrete units suitable for human and animal subjects and packaged individually as is known in the art.

As used herein, the terms "administering" and "administration" refer to any method of providing a compound or composition to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intraperitoneal injection, intravenous administration, intra-arterial administration, intramuscular administration, and subcutaneous administration. Administration can be continuous or intermittent.

In some embodiments of the presently-disclosed method, the PAK1 inhibitor is administered orally, topically, or by injection, including intramuscular and intraperitoneal injection. In some embodiments of the presently-disclosed method, the PAK1 inhibitor is administered by injection. In some embodiments, the PAK1 inhibitor is administered by intraperitoneal (i.p.) injection. In some embodiments, the PAK1 inhibitor is provided in a composition suitable for injection.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter is further illustrated by the following specific but non-limiting examples. The following examples may include compilations of data that are representative of data gathered at various times during the course of development and experimentation related to the present invention.

EXAMPLES

Deletion of one of two copies of the PMP22 gene causes hereditary neuropathy with liability to pressure palsies (HNPP). Deficiency of PMP22 in HNPP disrupts myelin junctions that seal the spaces between layers of myelin membrane. This disruption leads to "leaky" myelin that impairs the conduction of electrical signals on the nerves. This conduction failure results in neurological disabilities such as focal sensory loss or limb paralysis. In the studies described in these examples, a HNPP mouse model (Pmp22+/−), was used to identify a molecular pathway responsible for the disruption of myelin junctions. The results showed an increase of actin polymerization in the areas where myelin junctions resided. This increase was associated with an up-regulation of PAK1 activity, a kinase function that is known to regulate actin polymerization. HNPP mice were treated with PAK1 inhibitors. In the case of a particular inhibitor, treatment completely prevented the progression of nerve conduction failure and HNPP pathology. This work offers a promising therapeutic approach for HNPP. Moreover, myelin junction disruption takes place long before the actual stripping of myelin (demyelination) in the late phase of HNPP. Therefore, these findings provide a mechanism upstream to segmental demyelination, a pathological process relevant to many demyelinating diseases.

Results

Disruption of Myelin Junctions Takes Place Long Before Segmental Demyelination Seen in the Late Stage of Pmp22+/− Mice.

Figure 2:
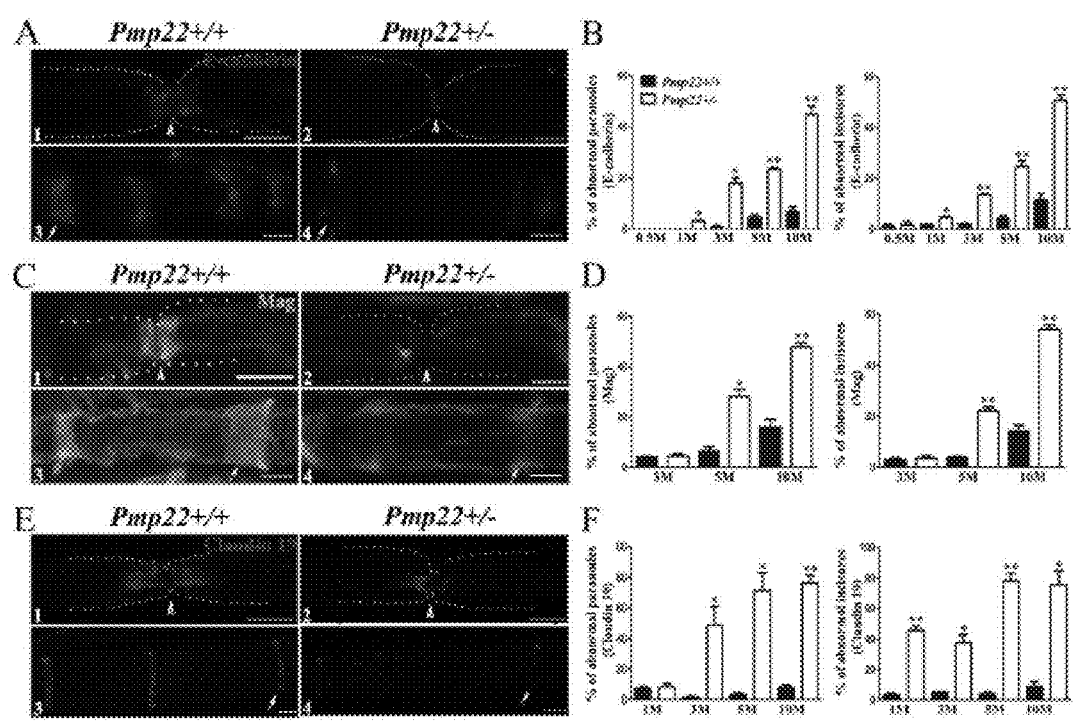
FIG. 2. includes data showing disruption of myelin junctions in Pmp22+/− nerves during aging. Paraffin sections of mouse sciatic nerves were stained with antibodies. Percentages of abnormal paranodes or incisures were manually counted [3]. An abnormal paranode or incisurae was defined as the staining was absent in more than a half of normally stained paranodal or incisure territory. Panel A of FIG. 2 shows E-cadherin antibody-stained paranodes in 3-month-old Pmp22+/+ mouse nerve fiber (stained areas adjacent to the node marked by an arrowhead in quadrant A1) but showed no signal in Pmp22+/− paranodes (quadrant A2). White dots outline the margin of the nerve fiber, based on its phase-contrast image. A strong E-cadherin band at the Pmp22+/− node (arrowhead in quadrant A2) was presumably due to an ectopic expression in Schwann cell microvilli. E-cadherin antibodies also stained Pmp22+/+ incisures (arrow in quadrant A3) but showed minimal signals in Pmp22+/− incisures (arrow in quadrant A4). Scale bars=10 μm. As shown in Panel B of FIG. 2, there was a significant increase of abnormal E-cadherin-stained paranodes and incisures from 1 month of age onward (n=140-340 paranodes and 800-1,700 incisures from either 3 Pmp22+/+ or 3 Pmp22+/− mice at each age group). *P<0.01, ** P<0.0001. As shown in Panel C of FIG. 2, Mag staining was present in the paranodes (quadrant C1) and incisures (arrow in quadrant C3) of 5-month-old Pmp22+/+ nerves but decreased in Pmp22+/− paranodes (quadrant C2) or incisures (arrow in quadrant C4). Scale bars=10 μm. As shown in Panel D of FIG. 2, there was a significant increase of abnormal Mag-stained paranodes or incisures from 5 month of age onward (n=160-300 paranodes and 900-1,500 incisures from 3 Pmp22+/+ and 3 Pmp22+/− mice at each age group). *P<0.01, ** P<0.0001. As shown in Panel E of FIG. 2, teased sciatic nerve fibers of Pmp22+/+ mice at the 3 months of age were stained with antibodies against claudin-19 to show paranodes (quadrant E1) and incisures (arrowhead in quadrant E3). The staining was reduced in Pmp22+/− paranodes (quadrant E2) and incisures (quadrant E4). Scale bars=10 μm. As shown in Panel F of FIG. 2, there was a significant difference found in paranodes from 3 months of age onward and in incisures from 1 month of age onward (n=280-380 paranodes and 800-1,200 incisures from 3 Pmp22+/+ and 3 Pmp22+/− mice at each age group). *P<0.01, ** P<0.0001.

While the disruption of myelin junctions in Pmp22+/− nerves has been described [3], the disruption had yet been evaluated during aging. In this study, dislocation of E-cadherin (marker for adherens junction), Mag (marker for transmembrane protein of paranodal loop), and claudin-19 (marker for tight junction) in Pmp22+/− paranodes and incisures from 2 weeks to 10 months of age were found (FIG. 2). Under electron microscopy, junction abnormalities with paranodal lamina splitting were qualitatively observed in Pmp22+/− nerves. In line with previous studies [3, 8], localization of Caspr and neurofascin at septate junctions was unchanged. Note that the total amounts of these junction proteins were not altered in Pmp22+/− nerves by Western blot [3]. Taken together, myelin junctions in Pmp22+/− nerves were abnormally formed during development and disrupted in adulthood. This abnormality was observable as early as 2 weeks, which was months ahead of segmental demyelination seen only after 10-12 months of age [3, 8].

Results above predict action potential propagation failure in a subset of Pmp22+/− nerve fibers with no segmental demyelination but severely increased myelin permeability [1]. Nerve conduction studies (NCS) were performed in mice at ages of 2, 6, and 12 months. There was a significant reduction of compound muscle action potential (CMAP) amplitudes in all age-groups of Pmp22+/− mice compared with those in Pmp22+/+ mice. In contrast, conduction velocities were not altered in Pmp22+/− nerves. To determine whether the decrease of CMAP was due to axonal loss, sciatic nerve morphometric analysis was performed at ages of 1, 3 and 6 months. The numbers of myelinated nerve fibers were not significantly different between Pmp22+/+ and Pmp22+/− mice. These findings do not support axonal loss.

To directly evaluate conduction block, sciatic nerves were surgically exposed to eliminate technical variations in NCS (FIGS. 3A, 3B and 3C). Conduction block (FIGS. 3D and 3E) was detected in 12 out of 17 studied Pmp22+/− mice but not found in any Pmp22+/+ mice. The remaining 5 Pmp22+/− mice had at least one of the three abnormalities— prolongation of distal latency (FIG. 3F), temporal dispersion (FIG. 3G), or both. Therefore, conduction block was present in Pmp22+/− nerves. This explains the decrease of CMAP amplitudes in Pmp22+/− mice.

F-Actin is Increased in Pmp22+/− Nerves and Co-Localized with Myelin Junctions.

Figure 4:
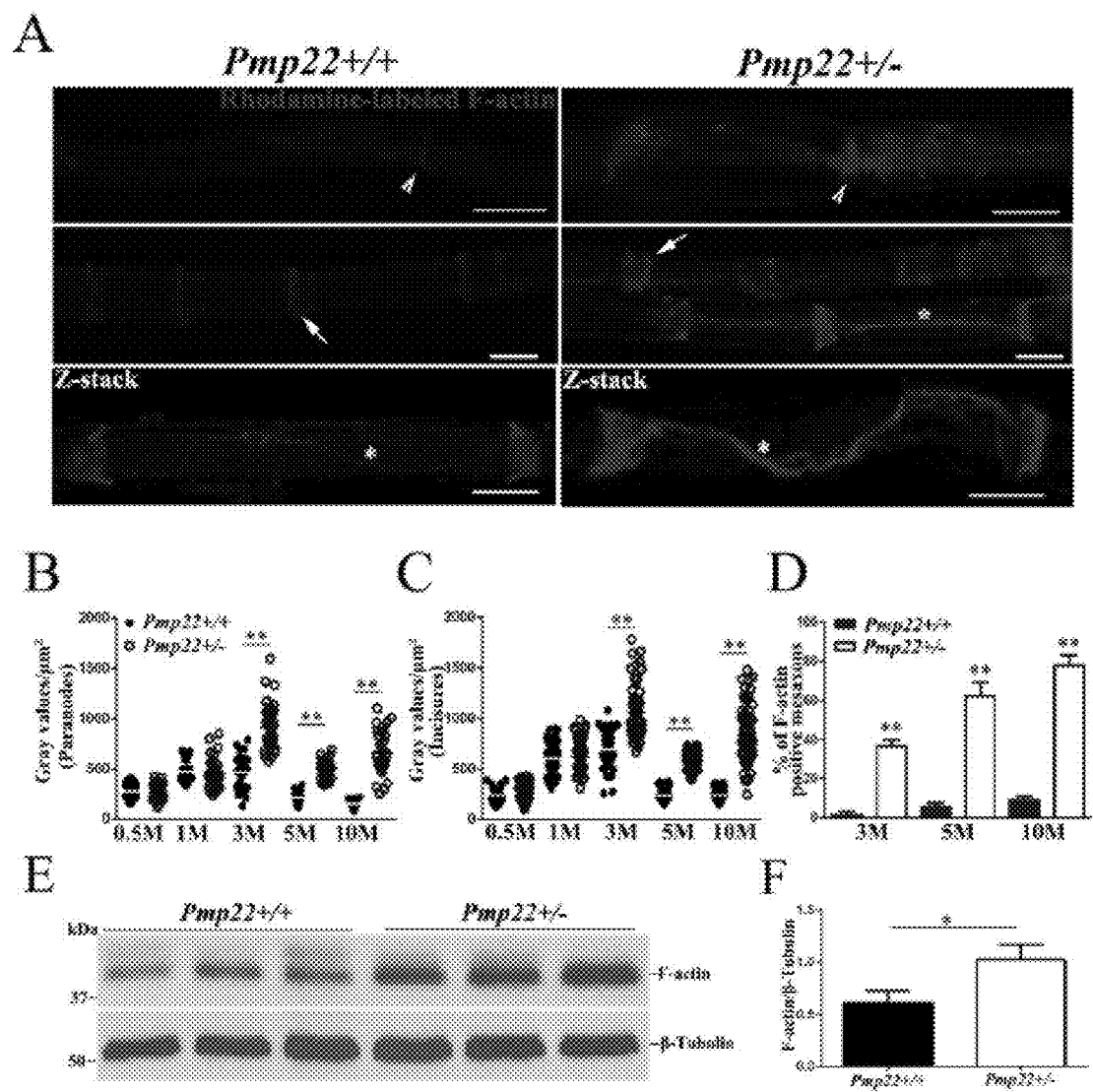
FIG. 4. includes data showing abnormally increased actin polymerization in the regions where myelin junctions reside. As shown in Panel A of FIG. 4, teased nerve fibers of mouse sciatic nerves were stained with fluorescent phalloidin, which was localized at nodes (arrowheads), incisures (arrows) and mesaxons (asterisks). F-actin was strongly expressed in Pmp22+/− nerves. Images in the $3^{rd}$ row were taken under confocal microscopy. The maximal projection of z-stack images was presented to show the mesaxon changes of F-actin at different layers. Scale bars=10 µm. As shown in Panels B and C of FIG. 4, fluorescence intensity was quantified by placing 2.5 µm×2.5 µm interest box 10 µm away from the node of Ranvier and by including the entire area of every incisures. The intensity of F-actin staining was increased in Pmp22+/− paranodes and incisures from 3 months of age onward (n=40-50 paranodes, 60-70 incisures from 3 Pmp22+/+ and 3 Pmp22+/− mice at each age group).  P<0.0001; M=month. As shown in Panel D of FIG. 4, the mesaxons with clearly visible F-actin-staining (asterisk in Pane A) were counted in teased nerve fibers of Pmp22+/+ and Pmp22+/− mice. The F-actin stained mesaxons in Pmp22+/− mice were increased from 3 month of age onward (n=75 mesaxons from 3 Pmp22+/+ and 3 Pmp22+/− mice at each age group).  P<0.0001; M=month. Panel E of FIG. 4 includes Western blot analysis of F-actin was performed in the sciatic nerves of 3 month-old Pmp22+/+ and Pmp22+/− mice. As shown in Panel F of FIG. 4, the levels of F-actin were significantly increased in Pmp22+/− nerves, compared with those in Pmp22+/+ nerves. *P<0.05. As shown in Panel G of FIG. 4, Pmp22+/+ and Pmp22+/− sciatic nerve explants were cultured for 3 hours in the presence of jasplakinolide (Jas) and double-stained with fluorescent phalloidin and an anti-Pan-Neurofascin antibody to label incisures. A group of explants was washed following Jas treatment and cultured for another 6 hours in jasplakinolide-free medium. The newly formed F-actin was strongly increased in Box 6 of Panel G of FIG. 4. Scale bars=10 µm. As shown in Panel H of FIG. 4, fluorescence intensity was quantified by including the entire area of each incisures. The intensity of new F-actin was increased in 3 month-old Pmp22+/− incisures, compared with those in Pmp22+/+ nerve fibers (n=120 incisures from 3 Pmp22+/+ and 3 Pmp22+/− mice; Scale bars=5 µm). ** P<0.0001.

F-actin is a common "denominator" in all types of junction complexes (FIG. 1B) for junction stabilization [12]. An altered actin polymerization in PMP22 deficiency was contemplated. Teased mouse nerve fibers were stained with rhodamine-conjugated phalloidin known to specifically label F-actin [14]. F-actin was localized in non-compact myelin regions (FIG. 4A) where myelin junctions also reside (FIGS. 1 and 2). Quantification of F-actin fluorescence intensity showed a significant difference between Pmp22+/+ and Pmp22+/− nerves from 3 to 10 months of age (FIGS. 4B, 4C and 4D). Moreover, Western blot confirmed the increase of F-actin in Pmp22+/− nerves (FIGS. 4E and 4F).

Dynamics of F-actin formation was tested as described [14]. Jasplakinolide is a membrane permeable cyclo-depsipeptide that competes with phalloidin for F-actin binding. After saturating the existing F-actin with jasplakinolide, phalloidin only labeled newly formed F-actin. Pmp22+/− nerves showed a higher level of new F-actins than that in Pmp22+/+ nerves (FIGS. 4G and 4H).

Activity of PAK1 is Increased in Pmp22+/− Nerves.

Figure 5:
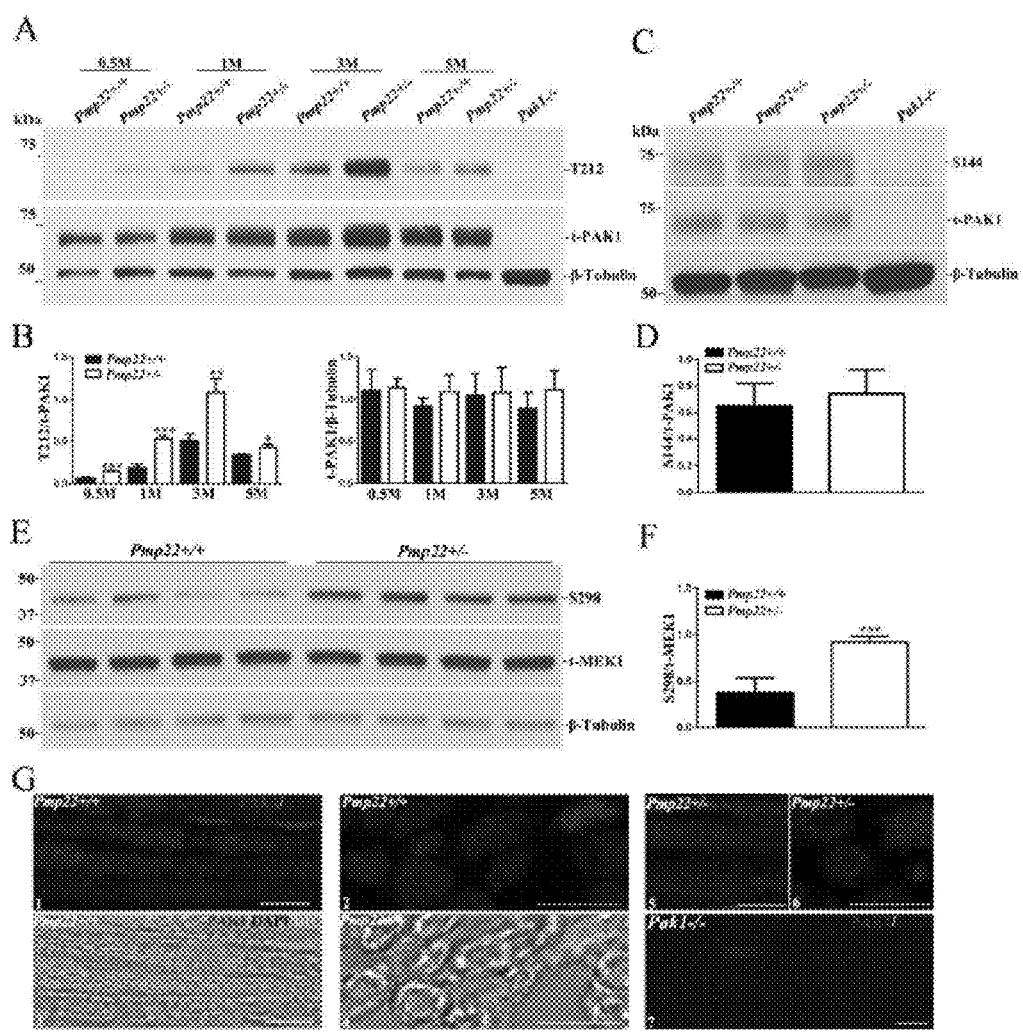
FIG. 5. includes data showing PAK1 activity is increased in Pmp22+/− nerves. Panel A of FIG. 5 includes Western blot of phosphorylated PAK1 (T212) and total PAK1 (t-PAK1) in the sciatic nerves from 0.5-5 month-old Pmp22+/+ and Pmp22+/− mice. Both T212 and t-PAK1 were not detectable in the sciatic nerves of Pak1−/− mice (line 9). With reference to Panel B of FIG. 5, T212 level was normalized against t-PAK1 levels. T-PAK1 level was normalized against β-Tubulin levels. The levels of T212, but not t-PAK1 levels, were significantly increased in Pmp22+/− nerves, compared with those in Pmp22+/+ nerves. *P<0.05,  P<0.01, * P<0.001. Panel C of FIG. 5 includes Western blot of S144 in the sciatic nerves of 3 month-old Pmp22+/+ and Pmp22+/− mice. S144 were not detectable in the sciatic nerves of Pak1−/− mice (line 4). With reference to Panel D of FIG. 5, S144 levels were normalized against t-PAK1 levels. S144 level was not significantly different between Pmp22+/+ and Pmp22+/− nerves. Panel E of FIG. 5 includes Western blot for phosphorylated MEK1 (S298) and total MEK1 (t-MEK1) in the sciatic nerves of 3 month-old Pmp22+/+ and Pmp22+/− mice. As shown in Panel F of FIG. 5, S298 levels were normalized against t-MEK1 levels. S298 levels were significantly increased in Pmp22+/− nerves, compared with those in Pmp22+/+ nerves. *** P<0.001. As shown in Panel G of FIG. 5, longitudinal (G1, G5) and transverse (G2, G6) sections of sciatic nerves were stained with antibodies against PAK1. The staining was superimposed with phase-contrast images (G3, G4), which showed PAK1 located in myelin and axons. PAK1 were not detectable in the sciatic nerves of Pak1−/− mice (G7). Scale bars=10 µm.

Alteration of actin polymerization prompted us to examine changes of F-actin's regulators such as Cdc42, Rac1, and PAK1 [15]. Both Cdc42 and Rac1 are functionally essential. Removal of either Cdc42 or Rac1 results in severe dysmyelination [16], which makes the two molecules unfavorable targets of intervention. In contrast, constitutive knockout of PAK1 (Pak1−/−) produces negligible phenotype in mice [17]. Normal morphology, electrophysiology, and functions in Pak1−/− peripheral nerves were also confirmed. Yet, this kinase has been shown to play roles in actin polymerization and cellular focal adhesion [15]. In mouse sciatic nerves, PAK1 (FIG. 5A), and PAK2 but not PAK3, were detected. Levels of total PAK1 (FIGS. 5A and 5B) or PAK2 were not different between Pmp22+/+ and Pmp22+/− nerves. Immunostaining with antibodies against total PAK1 showed diffuse distribution in the sciatic nerves similarly between Pmp22+/+ and Pmp22+/− mice (FIG. 5G).

PAK1-3 activation involves autophosphorylation at multiple amino acid residues, including S144, S199, and/or T423 [15]. In addition, PAK1, not PAK2-3, can be phosphorylated at T212 to activate PAK1 independently of small GTPases and regulate F-actin formation [18]. A Western blot of sciatic nerve lysates showed a significantly increased level of T212 (but not S144) in Pmp22+/− nerves compared with that in Pmp22+/+ nerves (FIGS. 5A and 5B). The activity of PAK1 reached its peak at age of 3-month-old, which correlated with the time when tomacula are actively formed [8]. The specificity of total PAK1, S144, and T212 antibodies was verified using Pak1+/+ and Pak1−/− nerves. All antibodies detected PAK1 in Pak1+/+ nerves but not in Pak1−/− nerves (FIGS. 5A and 5C).

PAK1 has been shown to phosphorylate MAPK kinase-1 (MEK1) at its S298 residue [19]. Western blot revealed an increase of phosphorylated MEK1 in Pmp22+/− nerves compared with that in Pmp22+/+ nerves (FIGS. 5E and 5F). Together, these data support an increase of PAK1 activation in PMP22 deficient nerves. Residues in other PAKs could be phosphorylated but cannot be substantiated due to the lack of specific antibodies.

PAK1 is Associated with Junction Protein Complexes

Both T212 and S144 antibodies failed to stain mouse nerves in the immunofluorescence experiments. To determine whether PAK1 is associated with junction protein complexes, co-immunoprecipitation (co-IP) was performed in mouse sciatic nerve lysates and verified interactions between E-cadherin, catenin and p120 (protein elements of adherens junction) (FIGS. 6C, 6D and 6E) [20]. Next, by using β-catenin antibodies, PAK1 was able to be pulled down from the sciatic nerve lysates (FIG. 6E). Because β-catenin is known to reside in the non-compact myelin regions and is an element of myelin adherens junction complex [20], PAK1 would associate with adherens junction protein complex. This finding is also consistent with a previously published study showing interactions between PAK1 and β-catenin [21].

To understand how PAK1 is activated in Pmp22+/− myelin, whether the disruption of adherens junction protein complex activates PAK1 was tested. The presence of adherens junction protein complex was verified in culture Schwann cells. By using siRNA, β-catenin and p120 were knocked down in culture Schwann cells. PAK1 activity indexed by T212 was increased in either β-catenin or p120 knock-down cells compared with that in control cells treated with scramble siRNA (FIGS. 6F1, 6F2, 6G1 and 6G2). Together, these findings suggest that PAK1 is present in the junction protein complexes. PAK1 may be activated when the junction protein complex is not formed normally.

To determine how PMP22 deficiency affects adherens junctions, an interaction between PMP22 and E-cadherin was contemplated. This speculation was based on the previous study showing interactions between PMP22 and other junction proteins with Ig or Ig-like extracellular domains [3]. HA- or GFP-tagged PMP22 and E-cadherin were co-expressed in 293a cells. The co-IP showed an interaction between PMP22 and the extracellular domain of E-cadherin (FIGS. 6A and 6B). When co-IP was done in mouse sciatic nerve lysates, interactions between endogenous PMP22 and E-cadherin were only detectable in mice younger than postnatal day 15 but not in adult nerves (FIG. 6C). This is in agreement with the immunostaining showing that PMP22 was localized into non-compact myelin regions in developing nerves but confined to internodal compact myelin and separated from myelin junctions in adult nerves [3]. These findings suggest that PMP22 might affect junction protein complex formation through its interactions with junction proteins during development. Abnormally formed junction complex would thereby activate PAK1.

Therapeutic Effect of PAK1 Inhibitor in Pmp22+/− Mice

Heterozygous deletion of PMP22 in patients with HNPP still leaves an intact allele of PMP22. The allele of PMP22 results in a partial production of PMP22 proteins [6], which would allow a portion of normal myelin junctions formed. It was reasoned that the activated PAK1 would further disrupt those normally formed junctions, presumably via alterations of actin polymerization. PF3758309 is a commercially available PAK inhibitor. Chow et al have tested this compound (25 mg/kg) in a skin cancer mouse model with a 7-10 day course of intraperitoneal (i.p.) injection [22]. The compound penetrated into the nervous system [23].

Figure 7:
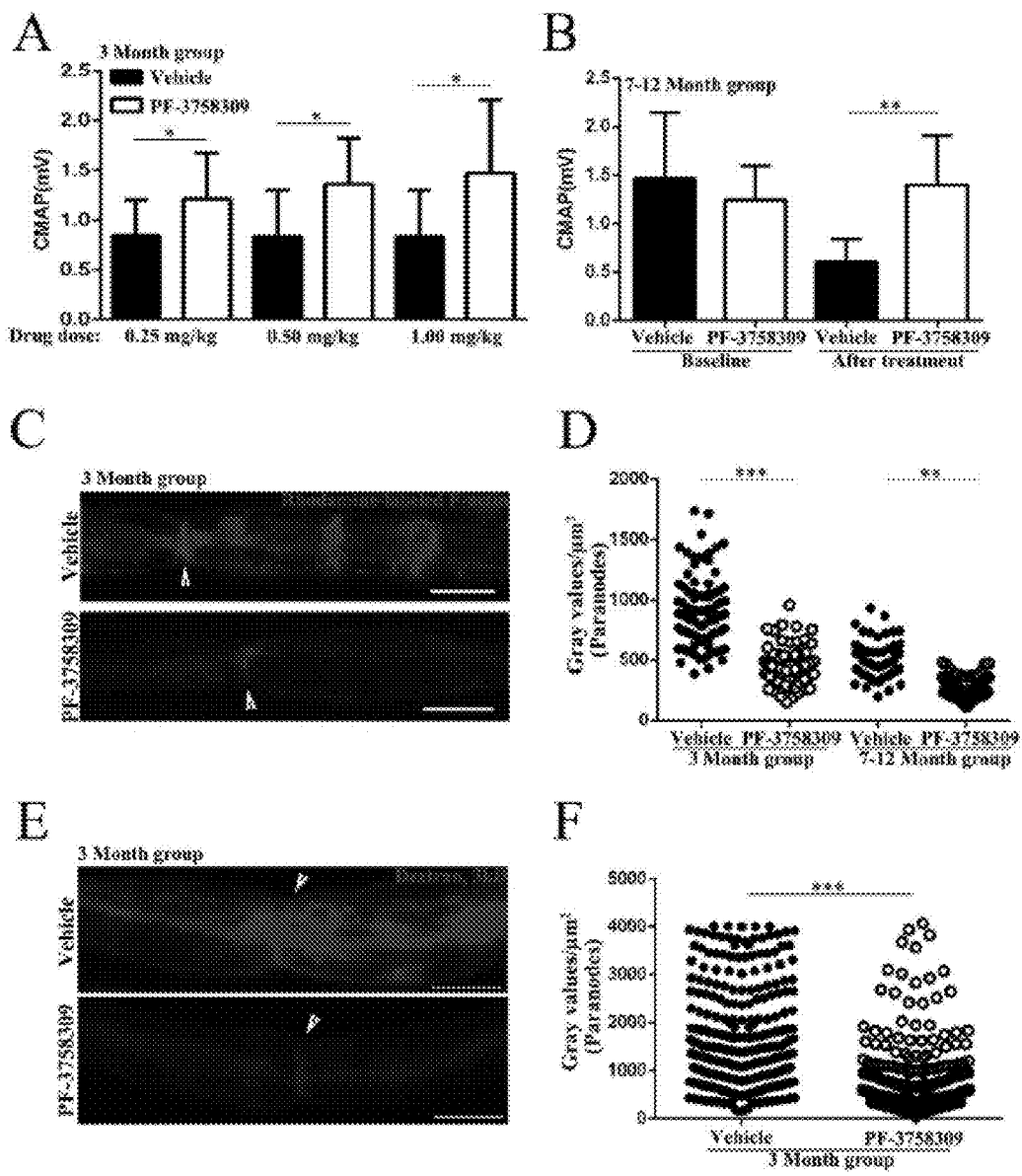
FIG. 7. includes data showing that a PAK1 inhibitor is therapeutic in Pmp22+/− mice. As shown in Panel A of FIG. 7, NCS on mouse sciatic nerves showed significantly higher CMAP amplitude in 3-month-old Pmp22+/− mice treated with 0.25-1.0 mg/kg PF-3758309 (n=42) for 11 weeks, compared with that in the vehicle group (n=24). There was a trend of dose-dependent change. *P<0.05. With reference to Panel B of FIG. 7, this difference of CMAP amplitudes was also found between 7-12-month-old Pmp22+/− mice treated with 0.25 mg/kg PF-3758309 and the vehicle group. CMAP was measured every 10 days. By the end of one month, CMAP amplitudes were already significantly different between the treated and vehicle groups. Thus, the treatment was stopped at this point. The baseline CMAP amplitudes prior to the treatment were not different between the two groups but decreased over the course of treatment in the vehicle group and unchanged in the PF-3758309 group.  P<0.01. With reference to Panel C of FIG. 7, teased nerve fibers from 3-month-old Pmp22+/− mice were stained with the fluorescence-phalloidin to reveal F-actin. A nerve fiber from a PF-3758309-treated mouse showed a lower intensity of F-actin fluorescence when compared with that in a nerve fiber from a vehicle-treated mouse. Arrowheads point to the node of Ranvier, which are flanked by paranodes on each side. Scale bars=10 μm. With reference to Panel D of FIG. 7, fluorescence intensity of F-actin staining was quantified by placing 2.5 μm×2.5 μm interest box 10 μm away from the node of Ranvier. The intensity was compared between the PF-3758309 treated group and the vehicle group (n=65-92 analyzed paranodes from 3 vehicle mice and 3 PF-3758309 treated mice). Note that a high level of F-actin in 3-month-old mice correlates well with a high level of PAK1 activity in the mice at the same age (FIG. 5A).  P<0.01, * P<0.001. With reference to Panel E of FIG. 7, sciatic nerve fascicles from 3-month-old Pmp22+/− mice were incubated with 3 kDa Dextran, as described [3], to evaluate the myelin permeability. Individual teased nerve fibers were imaged. Arrowheads point to the node of Ranvier. Notice that a nerve fiber from a mouse treated with vehicle showed higher fluorescence intensity than that in a nerve fiber from a mouse treated with PF-3758309. Scale bars=10 μm. With reference to Panel F of FIG. 7, fluorescence intensity was quantified by placing a 2.5 μm×2.5 μm interest box 10 μm away from the middle point of the node of Ranvier. The intensity was significantly decreased in 3-month-old PF-3758309-treated nerve fibers, compared to those from the vehicle group (n=495-521 analyzed paranodes from 3 vehicle mice and 3 PF-3758309-treated mice). * P<0.001.

Mouse tolerance to PF3758309 (i.p. daily) was tested. The dose of 2.5 mg/kg or 25 mg/kg killed over 50% of 20 Pmp22+/− mice within 15 days with drastic reduction of body weight, but no death was found in 21 vehicle-treated Pmp22+/− mice. Thus, Pmp22+/− mice were treated with 0.25, 0.5, 1.0 mg/kg PF3758309 or vehicle—saline (FIG. 7 and Table 1). Animals tolerated these doses well with no change of body weight or increase of death. To give a sufficient time for recovery of myelin permeability, the compound was injected for 11 weeks. Injection started at age of postnatal day 7. The treatment prevented the decline of CMAP amplitudes with all three dosages (FIG. 7A), but did not restore the CMAP amplitudes to the levels in Pmp22+/+ mice (3.2±0.6 mV in ten 3-month-old Pmp22+/+ mice versus 1.5±0.8 mV in eight 3-month-old Pmp22+/− mice treated with 1.00 mg/kg PF-3758309). The remaining outcomes were collected only from mice treated with the lowest dose of 0.25 mg/kg. PF3758309 suppressed levels of T212, Two additional PAK inhibitors (FRAX597 and FRAX486) were commercially available. However, they failed to inhibit PAK1 activity in mouse peripheral nerves (data not shown) and were not suitable for the treatment. This failure was presumably due to the poor penetrance into the peripheral nerve system.

TABLE 1

PAK1 inhibitor PF-3758309 is therapeutic in the Pmp22+/− mice 1 week old at start of injection (prior to tomacula formation)

|  | mouse number | drug dose | CV(m/s) | Ratio (T212/PAK1) | % Tomacula | % abnormal Claudin-19 | Ratio (S298/MEK1) |
|---|---|---|---|---|---|---|---|
| Vehicle | n = 8 (4F/4M) | 0.25 mg/kg/day; via I.P.; | 20.3 ± 1.5 | 0.75 ± 0.0 | 35.8 ± 5.5 | 55.7 ± 16.6 [a] 39.5 ± 4.5 [b] | 0.90 ± 0.1 |
| PF-3758309 | n = 8 (3F/5M) | duration = 11 weeks | 17.8 ± 3.0 | 0.61 ± 0.0 | 27.3 ± 4.5 | 36.5 ± 18.4 [a] 27.7 ± 4.6 [b] | 0.39 ± 0.2 |
| P value |  |  | 0.069 | 0.015 | 0.028 | 0.045  0.010 | 0.004 |

6-11 month age at start of injection (after tomacula reached their peak prevalence)

|  | mouse number | drug dose | CV(m/s) | Ratio (T212/PAK1) | % Tomacula +outlier | % Tomacula −outlier | % abnormal Claudin-19 |
|---|---|---|---|---|---|---|---|
| Vehicle | n = 8 (3F/5M) | 0.25 mg/kg/day; via I.P.; | 24.6 ± 3.4 | 0.34 ± 0.1 | 29.1 ± 3.0 | 29.1 ± 3.0 | 66.3 ± 8.7 [a] |
| PF-3758309 | n = 8 (4F/4M) | duration = 4 weeks [c] | 19.7 ± 11.1 | 0.26 ± 0.1 | 25.2 ± 7.5 | 22.8 ± 4.3 [d] | 43.5 ± 13.3 [a] |
| P value |  |  | 0.628 | 0.037 | 0.228 | 0.010 | 0.012 |

[a] Quantification of paranodes with abnormal claudin-19 staining.
[b] Quantification of incisures with abnormal claudin-19 staining.
[c] At the 4th week of injection, NCS already detected a significant difference. Thus, the treatment was terminated earlier than 12 weeks for this group of mice.
[d] An outlier was taken off from the PF-3758309 group.

phosphorylated MEK1 (S298) and F-actin (Table 1, FIGS. 7C and 7D), as well as improved abnormal claudin-19 distributions (i.e., tight junctions; Table 1) and myelin permeability (FIGS. 7E and 7F) compared with those in the vehicle group. Using teased nerve fibers, the percentages of nerve fibers with tomacula, a key pathology of HNPP, was quantified, as described [8]. Tomacula were fewer in the treated group (Table 1).

It is useful to determine whether the treatment is still effective after the developmental stage. Moreover, in human clinical trials, a range of ages, instead of a single age point, are usually included. Mice were enrolled at ages of 6-11 months. Again, F-actin levels were significantly lower in the PF3758309 (0.25 mg/kg) group (FIG. 7D). In FIG. 7, Panel B, CMAP amplitudes were measured prior to the treatment. After treatment, CMAP amplitudes decreased about a half (from 1.6±0.7 mV to 0.7±0.2 mV) in the vehicle group, but the decrease was completely prevented over the course of PF3758309 treatment. The measurement of baseline CMAP was not possible in the 1st set of experiment since the injection started at age of 1 week when mouse paws were too small for any reliable recording.

The percentages of tomacula in the 2nd set of experiment were not significantly different between PF3758309 and vehicle groups. However, there was one outlier with the highest percentage of tomacula (39.7%) in PF3758309 group. Another 14 Pmp22+/− mice (un-injected) were counted. None of them showed tomacula above 39.7%. When the outlier was removed, the difference of tomacula between PF3758309 and vehicle group was significant (the 6-7th column in Table 1). Finally, by Western blot, PAK1 activity indexed by T212 was decreased in PF3758309 groups compared with vehicle groups. The claudin-19 distribution was also improved in the treated group (Table 1).

PAK Inhibitor Suppresses F-Actin Formation Via PAK1

Suppression of F-actin formation by PF3758309 may not be due to PAK1 but an off-target effect. One may test this issue by crossing Pak1−/− into Pmp22+/− mice to remove Pak1 gene in Pmp22+/− mice. However, a compensation effect of PAK2 activity in Pak1−/− mice has been observed [24]. An increase of phosphorylated PAK2 (S20) in Pak1−/− Schwann cells (row 6 in FIG. 8) was confirmed. Thus, this approach does not help.

When Schwann cells were treated with either vehicle or PF3758309, F-actin became hardly detectable in Pak1+/+ cells. However, PF3758309 failed to change the levels of F-actin in Pak1−/− cells (row 1 in FIG. 8). This finding suggests that PF3758309 suppresses F-actin formation mainly via PAK1.

Figure 8:
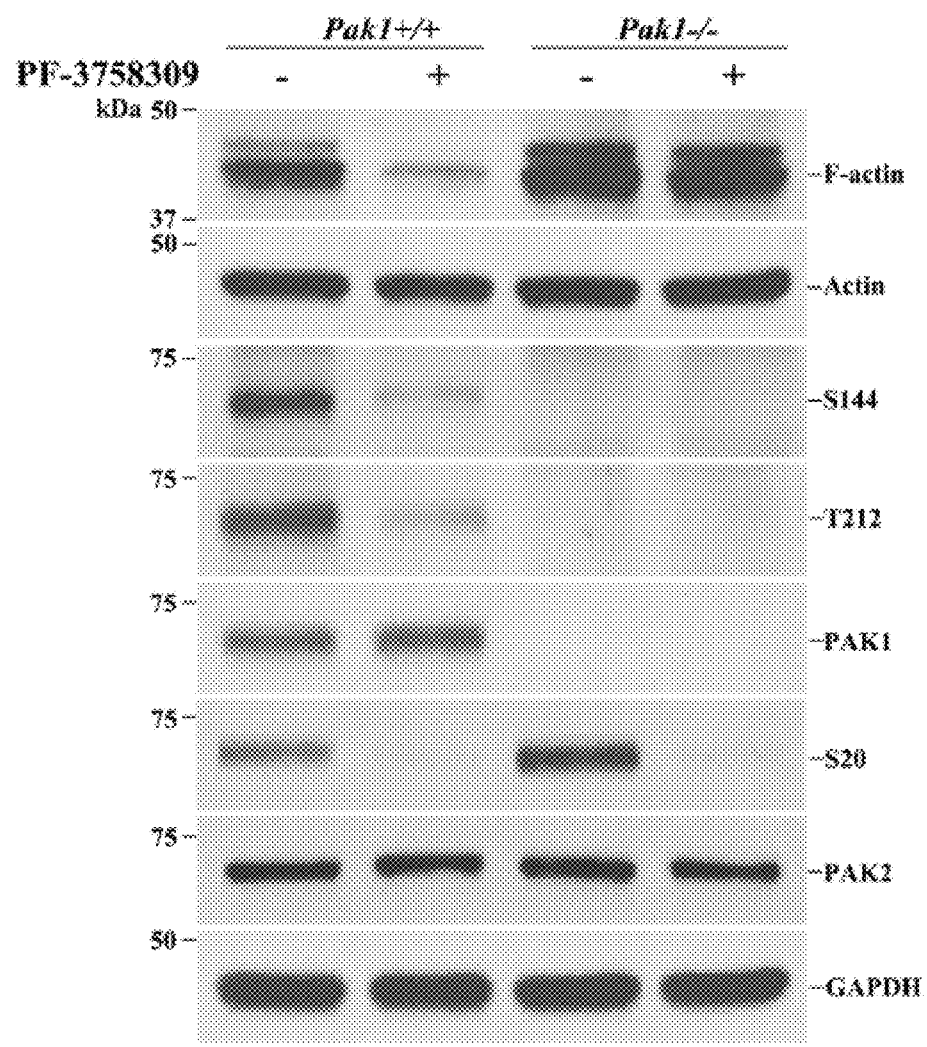
FIG. 8. Includes data showing that the PAK inhibitor PF-3758309 blocks actin polymerization via PAK1. F-actin, phosphorylated PAK1 (S144, T212) and phosphorylated PAK2 (S20) were analyzed in Pak1+/+ and Pak1−/− primary Schwann cell culture after the cells were treated with PF-3758309 (9 μM) for 12 hour. PF-3758309 suppressed the levels of F-actin, S144 and T212 in Pak1+/+ Schwann cells but failed to do so in Pak1−/− Schwann cells. The total actin and GAPDH were used as loading controls.

PF3758309 also inhibited the level of phosphorylated PAK2 (S20) while the total PAK2 levels were not altered by the compound (row 6 and 7 in FIG. 8). This suggests that PF3758309 is not a specific inhibitor for PAK1, but affects other PAKs.

Discussion

The study revealed a novel mechanism—myelin junctions are disrupted through PAK1 activity in HNPP mouse model. This change results in conduction block in the Pmp22+/− nerves, thereby explaining focal sensory/motor deficits in HNPP. Moreover, myelin junction disruption occurred much earlier than segmental demyelination in Pmp22+/− mice [3, 8, 9]. Therefore, functional demyelination represents an upstream mechanism prior to the actual stripping of myelin, a key pathology shared by many demyelinating diseases.

The conclusion above is supported by several lines of evidence. First, PAK1 activity indexed by T212 is increased in Pmp22+/− nerves. The time course of the PAK1-increase mirrors the progression of tomacula [8]. Second, based on the co-IP data, PAK1 interacts with adherens junction protein complexes either directly or indirectly, as demonstrated previously [21]. Interactions between PMP22 and other myelin-junction-related proteins have also been found in the previous study [3]. Because all myelin junctions are localized to the non-compact myelin regions [3], activated PAK1 would be available to affect other types of junctions and F-actin. T212 phosphorylation in PAK1 has been shown to recruit PAK1 to submembrane actins [18], where PAK1 activity may be further promoted by certain lipids, such as sphingosine or phosphoinositides, independent of small GTPases [25, 26]. Thus, an increase of T212 in Pmp22+/− nerves is highly relevant for F-actin formation locally around the myelin junctions.

This finding is consistent with numerous studies in epithelial cells that demonstrated junction disruption after altering actin polymerization [27, 28]. This finding is also in line with another study in transected mouse sciatic nerves; an increase of F-actin in myelin through the activation of a small GTPase, Rac1, promoted the removal of E-cadherin, a marker of adherens junctions. Inhibition of actin polymerization prevented the E-cadherin from being removed [14].

Interestingly, septate junctions are spared in Pmp22+/− nerves [3, 8], which was replicated in the present study. Like epithelial cells, myelinating Schwann cell polarizes into "apical-like and basolateral-like" domains [29]. Septate junctions are contemplated to be involved in a domain and mechanisms distinct from other junctions. Indeed, in the previous study [3], PMP22 was found in the paranodal regions during the early development but was not observed in the septate junction region.

Third, the PAK inhibitor (PF3758309) improved F-actin dysregulation, junction disruption, and abnormal myelin permeability in Pmp22+/− nerves. The decline of CMAP amplitudes was completely prevented by the PAK inhibitor, even in the adult nerves with fully developed pathology (FIG. 7 and Table 1). These results were from a large cohort of mice (total n=82 mice) of two age groups with three different dosages. Effective dose of PF3758309 (0.25 mg/kg) was 100 times lower than the dose of 25 mg/kg used in skin cancer mouse model [22].

Such a low dose of 0.25 mg/kg PF3758309 makes its use likely safer because of fewer off-target effects. Indeed, the mice were treated for 11 weeks, which was a long duration rarely seen in literature and far longer than the duration of 7-10 days used in the skin cancer mouse model [22]. Yet, there was no increase of mouse mortality and observable side-effect.

PAK inhibitor was effective in aged animals (6-11 month old; Table 1). While it is unlikely that any pharmacological treatment would be given to patients who are asymptomatic, this treatment of PAK inhibitor would still be effective after the patients become symptomatic with the pathology fully developed. This is in line with the previous observation of dynamic paranodal changes during action potential propagation in adult nerves [30]. Thus, PAK inhibitors may become a promising therapy option for HNPP.

The data show that PF-3758309 also inhibits PAK2 in the peripheral nerves. Thus, the beneficial effect in the treated Pmp22+/− mice could also relate to other types of PAKs, in addition to PAK1. Loss-of-function of PAK3 has been shown to affect synaptic plasticity [31]. Although the effective dose of PF-3758309 is very low in the study, it still remains to be determined whether the treatment results in any side-effects on cognitive functions.

Figure 3:
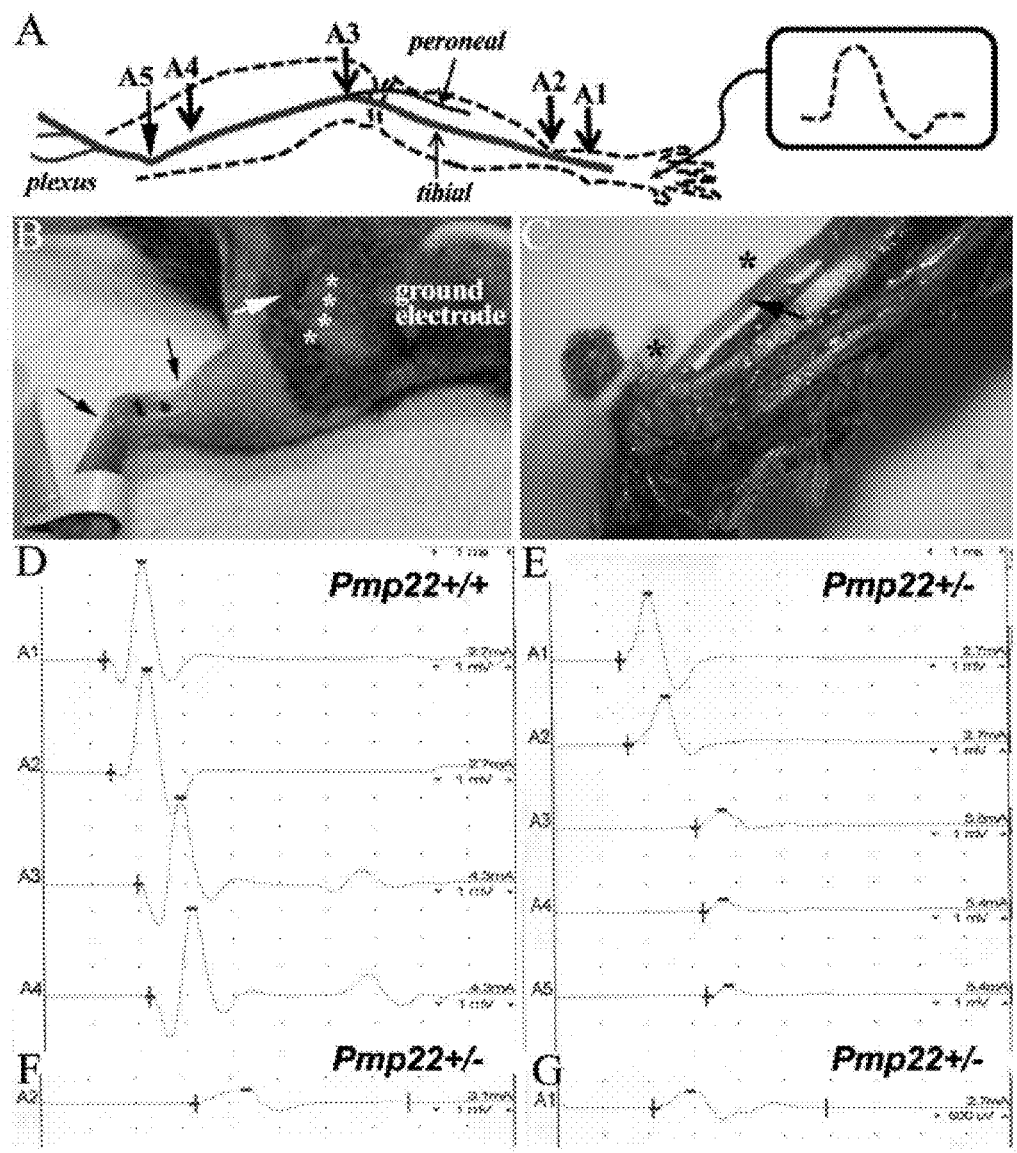
FIG. 3. includes data showing that a conduction block was detected in naïve Pmp22+/− nerves. As shown in Panel A of FIG. 3, a diagram shows the setting for the experiments. A1-5 indicates the sites where the stimulation electrodes were placed on surgically exposed sciatic nerve. As shown in Panel B of FIG. 3, in conventional NCS, proximal stimulation electrode is inserted blindly into the sciatic notch (white arrow in B). Variations of distances between the electrode and sciatic nerve (array of white asterisks) are not avoidable. This variation was eliminated by surgically exposing the sciatic nerves. Two black dots indicate the sites where distal stimulation electrodes were placed around ankle. As shown in Panel C of FIG. 3, area nearby ankle was dissected to reveal the tibial nerve (arrow in C). Due to the tiny space of this area, distance between the electrode and tibial nerve was highly consistent (two asterisks represent the sites of black dots in Panel B). Thus, it did not require surgical exposure to place the distal stimulation electrodes. Note that needle electrode at the asterisk sites was inserted just through the dermis to avoid any nerve injury. As shown in Panel D of FIG. 3, CMAP amplitudes were similar between A1 to A4. As shown in Panel E of FIG. 3, CMAP in a Pmp22+/− mouse at A3-A5 showed a >50% reduction of the A2 amplitude. This finding demonstrated a conduction block that was defined as a ≥50% decrease of proximal CMAP amplitude over the distal CMAP amplitude, a stringent criterion used in human NCS [39]. Conduction block was found in 12 out of 17 studied Pmp22+/− mice, but not in Pmp22+/+ mice. As shown in Panel F of FIG. 3, CMAP was recorded from a different mouse and showed a distal latency (3.3 ms) 2 times longer than that (1.2 ms) in Pmp22+/+ nerve (A2 in Panel D). The doubled distal latency was found in 2 mice out of the 17 Pmp22+/− mice, while the remaining 15 mice had variable degrees of prolonged distal latency. As shown in Panel G of FIG. 3, CMAP in this mouse had a duration of 4 ms (temporal dispersion) that was about twice longer than that in Pmp22+/+ nerve (A1 in Panel D). On average, the CMAP duration in 17 Pmp22+/− mice (3.9±1.7 ms) was significantly longer than that in 7 Pmp22+/+ mice (2.3±0.4 ms; p=0.001; 3-10 month old).

The severity of myelin permeability varied in different Pmp22+/− nerve fibers (FIG. 1B in Guo et al Ann Neurol 2014) [3]. This variability would produce two different populations of myelinated nerve fibers in HNPP. Those in the first group have severely "leaky" myelin (i.e., high capacitance), leading to failure of action potential propagation in the absence of demyelination (FIG. 3). Herein, this is called "functional demyelination". Inhibition of PAK1 is expected to restore the nerve conduction in the group of nerve fibers, which is reflected by the prevention of CMAP decline in PF3758309-treated Pmp22+/− mice (FIG. 7 and Table 1). Those in the second group have mildly increased permeability of myelin, which still allows action potentials to propagate but would partially compromise the safety factor of action potential propagation. This compromised safety factor would put the PMP22-deficient nerve fibers at risk to conduction failure if the fiber is challenged by external factors, such as mechanical stress. Indeed, the previous study has demonstrated that mechanical compression induced conduction block in Pmp22+/− nerves faster than that in Pmp22+/+ nerves [8]. It is not until the very late stage (>10-12 months) when obvious segmental demyelination and axonal loss start in Pmp22+/− mice [8, 32, 33]. Note conduction velocities in NCS are determined by large myelinated nerve fibers [1]. As long as there are some large myelinated nerve fibers still conducting action potentials in Pmp22+/− nerves, conduction velocities would remain normal or minimally decreased. This is also consistent with the observations in patients with HNPP [9].

Figure 6:
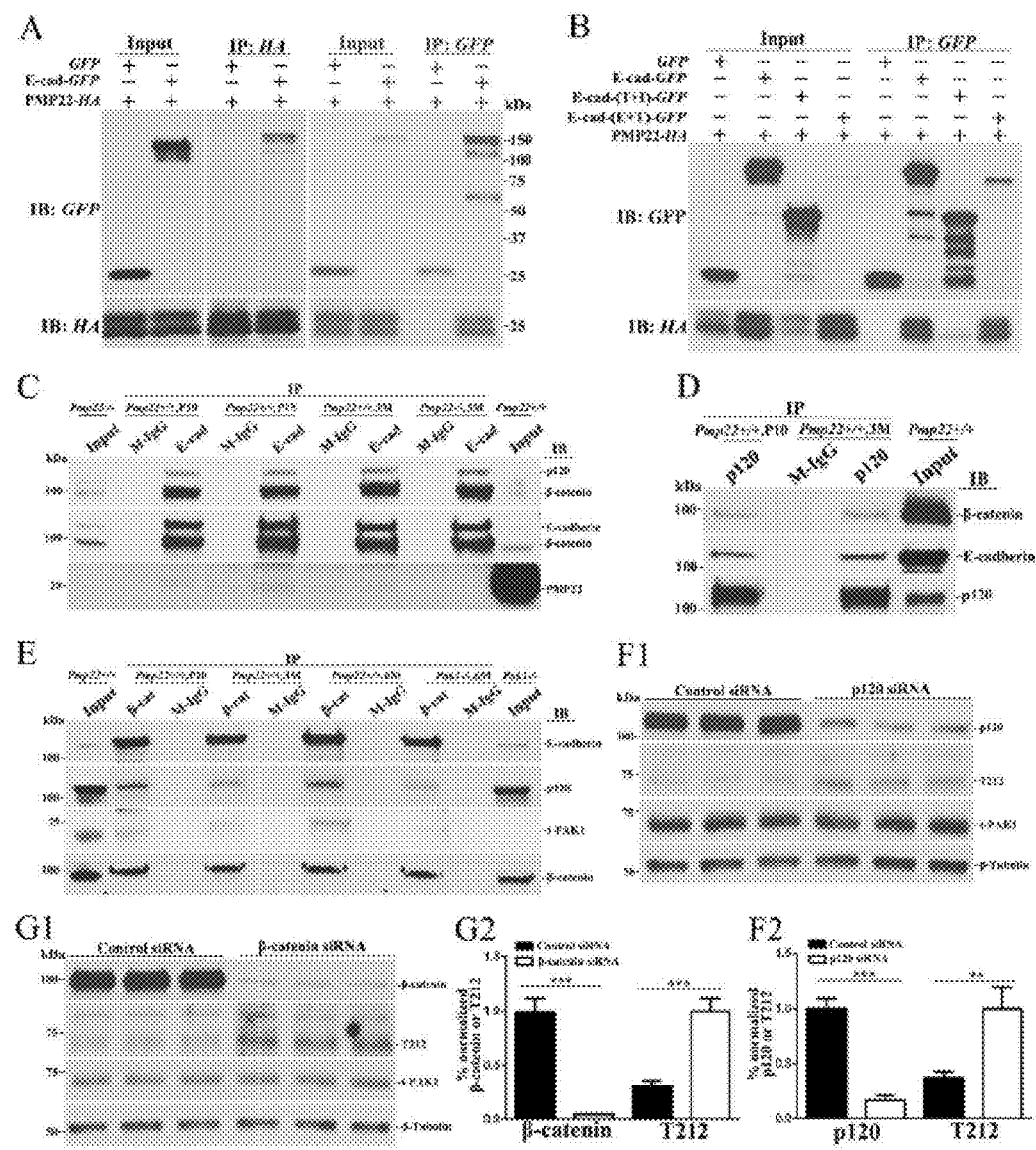
FIG. 6. includes data showing PAK1 complexes with adherens junction proteins and is activated after junction complex is disrupted. As shown in Panel A of FIG. 6, human HA-tagged PMP22 was co-expressed with GFP or GFP-tagged E-cadherin in HEK293a cells. Cell lysates were loaded as inputs and blotted with the anti-HA or anti-GFP antibodies (Input lanes). Lysates were immunoprecipitated and blotted with GFP or HA antibodies (IP lanes). A shown in Panel B of FIG. 6, GFP or GFP-tagged wild-type E-cadherin and mutants were co-expressed with HA-tagged PMP22 in HEK293a cells. Lysates were subjected to co-IP. IB=immunobltting; IP=immunoprecipitation. E+T=mutant with intracellular domain deleted, T+I=mutant with extracellular domain deleted. As shown in Panel C of FIG. 6, lysates were extracted from mouse sciatic nerves at postnatal days 10, 15 and 3 month-old Pmp22+/+ mice. Lysates were immunoprecipitated with anti-E-cadherin antibody and the precipitated endogenous proteins were blot with anti-PMP22, anti-β-catenin and anti-p120 antibody. E-cadherin antibodies were able to pull down PMP22 in P10 and 15 days Pmp22+/+ nerves, but failed to do so in 3-month-old Pmp22+/+ and Pmp22−/− nerves (negative control). Also, E-cadherin antibodies were able to pull down β-catenin and p120 in Pmp22+/+ nerves. IgG was used as another negative control. Note that the band of PMP22 was around 22 kDa, suggesting a major portion of the PMP22 proteins were glycosylated. With reference to Panel D of FIG. 6, IP using control IgG and anti-p120 antibody was carried out in extracts from mouse sciatic nerves at P10 and 3 month-old Pmp22+/+ mice. The presence of β-catenin and E-cadherin in these IP was evaluated by immunoblotting. The p120 antibodies were able to pull down β-catenin and E-cadherin in Pmp22+/+ sciatic nerves. With reference to Panel E of FIG. 6, immunoprecipitation using control IgG and anti-β-catenin antibodies was carried out using extracts from mouse sciatic nerves at P10, 3 and 6 month-old Pmp22+/+ mice. The presence of E-cadherin, p120, or PAK1 in this IP was evaluated by immunoblotting. The β-catenin antibodies were able to pull down E-cadherin, p120 and PAK1 in Pmp22+/+ sciatic nerves, but β-catenin failed to pull down PAK1 in Pak1−/− nerves. With reference to Panel F1 of FIG. 6, Schwann cells were transfected with p120 siRNA for 72 hours. Endogenous p120 and T212 were evaluated by immunoblotting. β-Tubulin was used as loading control. With reference to Panel F2 of FIG. 6, the p120 level was normalized against β-Tubulin level. T212 level was normalized against t-PAK1 level. Quantitative analysis showed an 85% knockdown of p120 level, compared to that in control siRNA. The levels of T212 were significantly increased in the p120-siRNA cells.  P<0.01, * P<0.001. With reference to Panel G1 of FIG. 6, Western blot analysis of T212 and PAK1 were performed in Schwann cells following transfection of β-catenin and control siRNAs. With reference to Panel G2 of FIG. 6, quantitative analysis shows a 95% knockdown of the β-catenin level. The levels of T212 were significantly increased in the β-catenin-siRNA cells. *** P<0.001.
Figure 9:
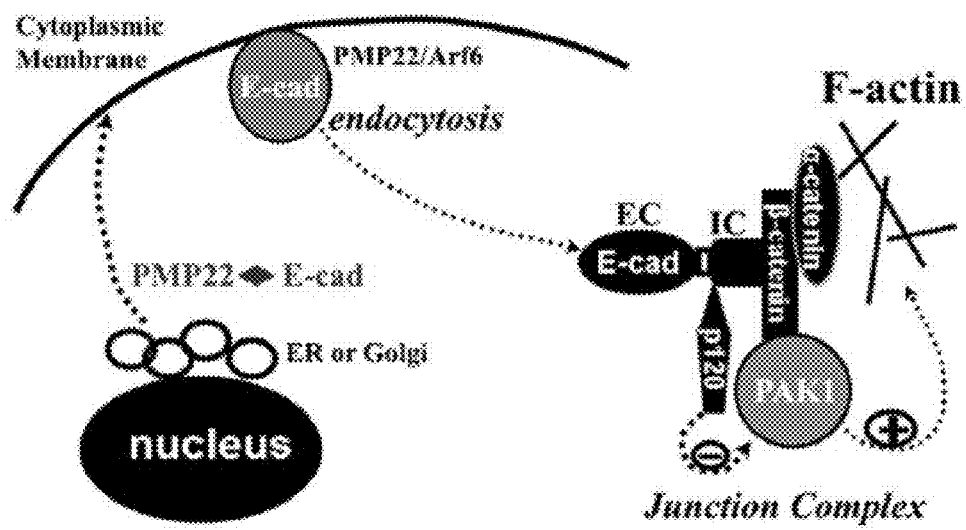
FIG. 9. Illustrates a mechanism for junction disruption in HNPP. Initiation—PMP22 and E-cadheren travel via the secretory pathway from endoplasmic reticulum (ER)/Golgi apparatus to cytoplasmic membrane [34, 35]. PMP22 has been reported to regulate the endocytosis of E-cadheren via Arf6 (an ATPase) [36]. PMP22 may also form a protein complex with E-cadherin during the secretory pathway. Deficiency of PMP22 would affect the transport processes of E-cadherin or other junction proteins, thereby leading to the abnormal formation of junction complex. Perpetuation—β-catenin in adherens junction protein complex has been shown to interact with PAK1 [21]. Abnormal formation of junction complex activates PAK1 in Pmp22+/− Schwann cells (FIG. 6B), which further promotes disruption of junction protein complexes. PAK1 is known to regulate actin polymerization [15]. Thus, activation of PAK1 may disrupt the junctions via actin polymerization.

In summary, a pathogenic mechanism of two steps is proposed—initiation and perpetuation (FIG. 9). Initiation: PMP22 and E-cadherin (or other junction proteins) travel via the secretory pathway from endoplasmic reticulum (ER)/Golgi apparatus to cytoplasmic membrane [34, 35]. Like the polarized epithelial cells, E-cadherin in developing Schwann cells has to be transported from apical domain (internodal membrane) to basolateral domain (paranode and incisures) through endocytosis [20, 35]. PMP22 has been reported to regulate the endocytosis of E-cadherin via Arf6, an ATPase [36]. PMP22 may affect E-cadherin transport during development (FIG. 6). In supporting this notion, the study has shown that PMP22 is transiently expressed in non-compact myelin regions of developing nerves but disappears in those compartments after maturation [3]. Because abnormal junction formation is upstream to the PAK1 activation, the PAK inhibitor would not affect this step. Perpetuation: HNPP with heterozygous deletion of PMP22 still have a normal allele that produces about a half of PMP22 proteins in normal controls [6]. These residual PMP22 proteins would permit some myelin junctions to form. However, after abnormal formation of the junction complex activates PAK1 (FIG. 6), PAK1 activity promotes junction disruption in adulthood (FIGS. 2 and 6). Thus, this junction disruption, not the abnormal junction formation during early development, would be affected by the PAK inhibitor. It still remains to be determined whether the junction disruption was through the increase of F-actin and/or via another unidentified pathway. However, studies in epithelial cells have demonstrated junction disruption by altering actin polymerization [27, 28]. After all, inhibition of PAK1 activity did suppress the formation of F-actin (FIG. 7C, 7D and FIG. 8). Together, these findings not only provide a mechanistic explanation for abnormal myelin permeability and impaired action potentials propagation in HNPP, but also offer a promising therapeutic approach for this disease.

Materials and Methods

Animals and Drug Administration

Pmp22+/− mice were backcrossed with C57Bl6J mice (Jackson Lab) for more than 10 generations to reach congenic. Mice were genotyped as described [7]. The congenic Pmp22+/− mice have been extensively characterized [3]. They showed pathology and other features similar to those in Pmp22+/− mice with mixed background (C57Bl6J/129) [8].

Pak1−/− mice were from Dr. Jonathan Chernoff's lab, Fox Chase Cancer Center, USA. The Pak1−/− mice were produced in C57Bl6J background and have been described with negligible phenotype [17]. All mice were housed in Tennessee Valley Healthcare System (TVHS) animal facility, a part of Vanderbilt animal care system. Experimental procedures were approved by the IACUC of Vanderbilt University.

For PAK1 inhibitor (PF3758309) injections, Pmp22+/− mice were randomized into vehicle and treated groups. Based on the power calculation of variations derived from mouse compound nerve action potentials, 7 mice for each group would have a 92% chance to detect a significant difference. PF-3758309 (Cat# CT-PF0375, ChemieTek) was dissolved in normal saline for intraperitoneal injection (i.p.) daily.

Co-Immunoprecipitation

Sciatic nerves or cells were lysed in immunoprecipitation buffer (Cat#87788, Thermo scientific) with proteinase/phosphatase inhibitor cocktail and incubated with primary antibodies overnight at 4° C. with rotation (70 rpm). Protein G agarose beads (Cat#15920-010, Life technologies) were added for another 2 hour incubation at 4° C. Samples were eluted with Laemmli sample buffer (Cat#161-0737, Biorad), resolved by SDS-PAGE, and analyzed by immunoblot.

Evaluation of Myelin Permeability

This technique has been validated [3]. In brief, 1 cm sciatic nerve fascicles were submerged in artificial CSF after epineurium removal and sealed at both ends with Vaseline. A 3 kDa Dextran of fluorescence (2 mg/ml, Cat# D3329, Life technologies) was added for one hour incubation at room temperature without oxygenation. After washing, the nerve fascicles were fixed in 4% PFA for 10 minutes and teased into individual nerve fibers on glass slides for fluorescence microscopy. Fluorescence intensity was quantified by placing a 5 μm×5 μm interest box 10 μm away from the middle point of the node of Ranvier.

β-Catenin or p120 Knockdown in Schwann Cells

Silencing of β-catenin and p120 were carried out using Accell SMARTpool siRNAs (Cat# A-062106-13 and A-040628-15, Dharmacon). Schwann cells were transfected with 1 μM siRNA. The efficiency of the knockdown was evaluated by Western blot 72 hours after the transfection. Accell non-targeting siRNA (Cat# D-001910, Dharmacon) was used as negative control.

Immunofluorescence Staining

This method was modified from the published study [3, 8]. In brief, sciatic nerves were fixed, embedded in paraffin, and cut into 5 μm-thick slices. Sections were incubated overnight with primary antibodies at 4° C. After washing, sections were stained for 1 hour with secondary antibodies. The stained slides were examined under a Leica fluorescent microscope (Leica DM6000B). For teased nerve stains, sciatic nerves were fixed in 4% paraformaldehyde (PFA) overnight and teased into individual fibers on glass slides. The slides were dried overnight, reacted with primary antibodies, and followed by secondary antibodies. For newly formed F-actin staining, as described [14], the existing F-actin in sciatic nerve explants was saturated with a cell-permeable actin-binding compound, jasplakinolide (Cat#420127, Millipore), at 1 μM in culture media. After washing with PBS, the explants were incubated in a drug-free media for 6 hours at 37° C. The explants were fixed in 4% PFA and teased for F-actin staining using fluorescent phalloidin (1:400, Cat# R415, Life Technologies).

Nerve Conduction Study (NCS)

NCS was previously described [8]. In brief, mice were anesthetized with isoflurane (VetEquip Inc. Cat#908106; 1.7 L/minute of oxygen at 1.0 bar; 1.5% of the total oxygen flow being vaporized with Isoflurane). This anesthetic drug has been tested. It does not affect nerve conduction if the procedure is completed within 25 minutes. A skilled technician gets NCS done in each mouse within 6 minutes. For the experiments of conduction block in FIG. 3, Avertin (250 mg/kg, i.p.) was used for anesthesia. Avertin did not affect CMAP over 2 hours (unpublished observation). CMAP was recorded from the intrinsic foot muscle using needle electrodes. Stimulation electrodes were positioned percutaneously at the sciatic notch and adjacent to the tibial nerve at the ankle. CMAP amplitudes were measured from baseline to the peak of negative deflection.

Morphometric Analysis of Mouse Sciatic Nerves and Electron Microscopy with High Pressure Freezing This method has been described [37]. Epon sections (1 μM thickness) of mouse sciatic nerves were examined under the 63× objective. The entire field of transverse sections of each nerve was imaged for analysis. Images were imported into software (ImagePro Plus). Areas of each field were counted to obtain the number of nerve fibers.

Electron microscopy on mouse sciatic nerves was performed as described [38]. Briefly, sciatic nerves were cryo-fixed in a high-pressure freezer (HPM100; Leica) and freeze substitution was performed in an embedding system at low temperature (AFS; Leica) using the tannic acid-$OsO_4$ protocol. Samples were embedded in Epon, sectioned (Ultracut S Ultramicrotome, Leica), and stained with an aqueous solution of 2% uranyl acetate followed by lead citrate. Samples were examined in a LEO EM 912AB electron microscope (Zeiss, Oberkochen, Germany). Pictures were taken with an on-axis 2048×2048-CCD-camera (TRS, Moorenweis, Germany).

Western Blot

Chopped sciatic nerves were immediately dropped into RIPA buffer (Cat# R0278, Sigma) with proteinase/phosphatase inhibitor cocktail (Cat#5872, Cell Signaling). Samples were homogenized for protein isolation. Protein concentration was determined by BCA assay (Prod#23225, Thermo Scientific). Samples were loaded into SDS-PAGE gels and transferred to a PVDF membrane. The membranes were blotted with 5% non-fat milk and incubated overnight at 4° C. with primary antibodies, and followed by secondary antibodies. The immune complexes were detected by the enhanced chemoilluminescence (Cat# NEL103001, Perkin Elmer). In some cases, the blots were stripped and re-probed with additional antibodies. Quantification of band intensity was performed by the ImageJ software (rsbweb.nih.gov/ij/).

Plasmids and Transfection

E-cadherin-GFP plasmid was purchased from Addgene (Cat#28009). PMP22-HA was obtained from Genocopoia (Cat# EX-D0117-M06). The primers for E-cadherin pE-cad-(E+T)-GFP were, forward: 5'-CCCAAGCTTGCCAC-CATGGGCCCTTGGAGCCGC-3', reverse: 5'-CCGCTC-GAGAAACAGCAAGAGCAGCAGAATCAG-3'; pE-cad-(T+I)-GFP, forward: 5'-CGGGGTACCGCCACCATGATTCTGGGGATTCTTG-GAGG-3', reverse: 5'-CCGCTCGAGGTCGTCCTCGC-CGCCT-3'. The accuracy of all plasmids was verified by DNA sequencing. The plasmids were transfected into HEK293a cells by using Effectene (Cat#301425, Qiagen) according to the manufacturer's instructions.

Statistics

Statistical analysis was performed using GraphPad Prism software version 6.0 or SAS 9.4. The data was represented as the mean±SD. For normally distributed data, a Student t test was utilized. The Wilcoxon Rank-sum test was used when the data were not under normal distribution. Differences were considered significant when the P value was less than 0.05.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. Li J. Molecular regulators of nerve conduction—Lessons from inherited neuropathies and rodent genetic models. Exp Neurol. 2015; 267:209-18. Epub 2015/03/21. doi: 10.1016/j.expneurol.2015.03.009. PubMed PMID: 25792482; PubMed Central PMCID: PMC4417062.
2. Hartline D K, Colman D R. Rapid conduction and the evolution of giant axons and myelinated fibers. Curr Biol. 2007; 17(1):R29-35. Epub 2007/01/09. doi: 10.1016/j.cub.2006.11.042. PubMed PMID: 17208176.
3. Guo J, Wang L, Zhang Y, Wu J, Arpag S, Hu B, et al. Abnormal junctions and permeability of myelin in PMP22-deficient nerves. Ann Neurol. 2014; 75(2):255-65. Epub 2013/12/18. doi: 10.1002/ana.24086. PubMed PMID: 24339129; PubMed Central PMCID: PMC4206215.
4. Chance P F, Alderson M K, Leppig K A, Lensch M W, Matsunami N, Smith B, et al. DNA deletion associated with hereditary neuropathy with liability to pressure palsies. Cell. 1993; 72(1):143-51. Epub 1993/01/15. PubMed PMID: 8422677.
5. Nicholson G A, Valentijn L J, Cherryson A K, Kennerson M L, Bragg T L, DeKroon R M, et al. A frame shift mutation in the PMP22 gene in hereditary neuropathy with liability to pressure palsies. Nat Genet. 1994; 6(3): 263-6. Epub 1994/03/01. doi: 10.1038/ng0394-263. PubMed PMID: 8012388.
6. Li J, Ghandour K, Radovanovic D, Shy R R, Krajewski K M, Shy M E, et al. Stoichiometric alteration of PMP22 protein determines the phenotype of hereditary neuropathy with liability to pressure palsies. Arch Neurol. 2007; 64(7):974-8. Epub 2007/07/11. doi: 10.1001/archneur.64.7.974. PubMed PMID: 17620487.
7. Adlkofer K, Martini R, Aguzzi A, Zielasek J, Toyka K V, Suter U. Hypermyelination and demyelinating peripheral neuropathy in Pmp22-deficient mice. Nat Genet. 1995; 11(3):274-80. Epub 1995/11/01. doi: 10.1038/ng1195-274. PubMed PMID: 7581450.
8. Bai Y, Zhang X, Katona I, Saporta M A, Shy M E, O'Malley H A, et al. Conduction block in PMP22 deficiency. J Neurosci. 2010; 30(2):600-8. Epub 2010/01/15. doi: 10.1523/JNEUROSCI.4264-09.2010. PubMed PMID: 20071523; PubMed Central PMCID: PMC3676309.
9. Li J, Krajewski K, Shy M E, Lewis R A. Hereditary neuropathy with liability to pressure palsy: the electrophysiology fits the name. Neurology. 2002; 58(12):1769-73. Epub 2002/06/27. PubMed PMID: 12084875.
10. Poliak S, Matlis S, Ullmer C, Scherer S S, Peles E. Distinct claudins and associated PDZ proteins form different autotypic tight junctions in myelinating Schwann cells. J Cell Biol. 2002; 159(2):361-72. Epub 2002/10/31. doi: 10.1083/jcb.200207050. PubMed PMID: 12403818; PubMed Central PMCID: PMC2173042.
11. Itoh M, Furuse M, Morita K, Kubota K, Saitou M, Tsukita S. Direct binding of three tight junction-associated MAGUKs, ZO-1, ZO-2, and ZO-3, with the COOH termini of claudins. J Cell Biol. 1999; 147(6):1351-63. Epub 1999/12/22. PubMed PMID: 10601346; PubMed Central PMCID: PMC2168087.
12. Hartsock A, Nelson W J. Adherens and tight junctions: structure, function and connections to the actin cytoskeleton. Biochim Biophys Acta. 2008; 1778(3):660-9. Epub 2007/09/15. doi: 10.1016/j.bbamem.2007.07.012. PubMed PMID: 17854762; PubMed Central PMCID: PMC2682436.
13. Scheiermann C, Meda P, Aurrand-Lions M, Madani R, Yiangou Y, Coffey P, et al. Expression and function of junctional adhesion molecule-C in myelinated peripheral nerves. Science. 2007; 318(5855):1472-5. Epub 2007/12/01. doi: 10.1126/science.1149276. PubMed PMID: 18048693; PubMed Central PMCID: PMC3299566.
14. Jung J, Cai W, Lee H K, Pellegatta M, Shin Y K, Jang S Y, et al. Actin polymerization is essential for myelin sheath fragmentation during Wallerian degeneration. J Neurosci. 2011; 31(6):2009-15. Epub 2011/02/11. doi: 10.1523/JNEUROSCI.4537-10.2011. PubMed PMID: 21307239; PubMed Central PMCID: PMC3071261.
15. Bokoch G M. Biology of the p21-activated kinases. Annu Rev Biochem. 2003; 72:743-81. Epub 2003/04/05. doi: 10.1146/annurev.biochem.72.121801.161742. PubMed PMID: 12676796.
16. Benninger Y, Thurnherr T, Pereira J A, Krause S, Wu X, Chrostek-Grashoff A, et al. Essential and distinct roles for cdc42 and rac1 in the regulation of Schwann cell biology during peripheral nervous system development. J Cell Biol. 2007; 177(6):1051-61. Epub 2007/06/20. doi: 10.1083/jcb.200610108. PubMed PMID: 17576798; PubMed Central PMCID: PMC2064365.
17. Allen J D, Jaffer Z M, Park S J, Burgin S, Hofmann C, Sells M A, et al. p21-activated kinase regulates mast cell degranulation via effects on calcium mobilization and cytoskeletal dynamics. Blood. 2009; 113(12):2695-705. Epub 2009/01/07. doi: 10.1182/blood-2008-06-160861. PubMed PMID: 19124833; PubMed Central PMCID: PMC2661857.
18. Rashid T, Banerjee M, Nikolic M. Phosphorylation of Pak1 by the p35/Cdk5 kinase affects neuronal morphology. J Biol Chem. 2001; 276(52):49043-52. Epub 2001/10/18. doi: 10.1074/jbc.M105599200. PubMed PMID: 11604394.
19. Slack-Davis J K, Eblen S T, Zecevic M, Boerner S A, Tarcsafalvi A, Diaz H B, et al. PAK1 phosphorylation of MEK1 regulates fibronectin-stimulated MAPK activation. J Cell Biol. 2003; 162(2):281-91. Epub 2003/07/24. doi: 10.1083/jcb.200212141. PubMed PMID: 12876277; PubMed Central PMCID: PMC2172784.
20. Tricaud N, Perrin-Tricaud C, Bruses J L, Rutishauser U. Adherens junctions in myelinating Schwann cells stabilize Schmidt-Lanterman incisures via recruitment of p120 catenin to E-cadherin. J Neurosci. 2005; 25(13):3259-69. Epub 2005/04/01. doi: 10.1523/JNEUROSCI.5168-04.2005. PubMed PMID: 15800180.
21. He H, Shulkes A, Baldwin G S. PAK1 interacts with beta-catenin and is required for the regulation of the beta-catenin signaling pathway by gastrins. Biochim Biophys Acta. 2008; 1783(10):1943-54. Epub 2008/06/03. doi: 10.1016/j.bbamcr.2008.04.016. PubMed PMID: 18515095.
22. Chow H Y, Jubb A M, Koch J N, Jaffer Z M, Stepanova D, Campbell D A, et al. p21-Activated kinase 1 is required for efficient tumor formation and progression in a Ras-mediated skin cancer model. Cancer Res. 2012; 72(22): 5966-75. Epub 2012/09/18. doi: 10.1158/0008-5472.CAN-12-2246. PubMed PMID: 22983922; PubMed Central PMCID: PMC3500416.
23. Murray B W, Guo C, Piraino J, Westwick J K, Zhang C, Lamerdin J, et al. Small-molecule p21-activated kinase inhibitor PF-3758309 is a potent inhibitor of oncogenic signaling and tumor growth. Proc Natl Acad Sci USA. 2010; 107(20):9446-51. Epub 2010/05/05. doi: 10.1073/pnas.0911863107. PubMed PMID: 20439741; PubMed Central PMCID: PMC2889050.
24. Elsherif L, Ozler M, Zayed M A, Shen J H, Chernoff J, Faber J E, et al. Potential compensation among group I PAK members in hindlimb ischemia and wound healing. PloS one. 2014; 9(11):e112239. Epub 2014/11/08. doi: 10.1371/journal.pone.0112239. PubMed PMID: 25379771; PubMed Central PMCID: PMC4224450.
25. Strochlic T I, Viaud J, Rennefahrt U E, Anastassiadis T, Peterson J R. Phosphoinositides are essential coactivators for p21-activated kinase 1. Mol Cell. 2010; 40(3):493-500. Epub 2010/11/13. doi: 10.1016/j.molcel.2010.10.015. PubMed PMID: 21070974; PubMed Central PMCID: PMC3026281.
26. Zenke F T, King C C, Bohl B P, Bokoch G M. Identification of a central phosphorylation site in p21-activated kinase regulating autoinhibition and kinase activity. J Biol Chem. 1999; 274(46):32565-73. Epub 1999/11/07. PubMed PMID: 10551809.
27. Madara J L, Barenberg D, Carlson S. Effects of cytochalasin D on occluding junctions of intestinal absorptive cells: further evidence that the cytoskeleton may influence paracellular permeability and junctional charge selectivity. J Cell Biol. 1986; 102(6):2125-36. Epub 1986/06/01. PubMed PMID: 3711143; PubMed Central PMCID: PMC2114240.
28. Madara J L, Moore R, Carlson S. Alteration of intestinal tight junction structure and permeability by cytoskeletal contraction. Am J Physiol. 1987; 253(6 Pt 1):C854-61. Epub 1987/12/01. PubMed PMID: 3425707.
29. Ozcelik M, Cotter L, Jacob C, Pereira J A, Relvas J B, Suter U, et al. Pals1 is a major regulator of the epithelial-like polarization and the extension of the myelin sheath in peripheral nerves. J Neurosci. 2010; 30(11):4120-31. Epub 2010/03/20. doi: 10.1523/JNEUROSCI.5185-09.2010. PubMed PMID: 20237282.
30. Wurtz C C, Ellisman M H. Alterations in the ultrastructure of peripheral nodes of Ranvier associated with repetitive action potential propagation. J Neurosci. 1986; 6(11): 3133-43. Epub 1986/11/01. PubMed PMID: 3490547.
31. Boda B, Albert S, Nikonenko I, Node-Langlois R, Jourdain P, Moosmayer M, et al. The mental retardation protein PAK3 contributes to synapse formation and plasticity in hippocampus. J Neurosci. 2004; 24(48):10816-25. Epub 2004/12/03. PubMed PMID: 15574732.
32. Adlkofer K, Frei R, Neuberg D H, Zielasek J, Toyka K V, Suter U. Heterozygous peripheral myelin protein 22-deficient mice are affected by a progressive demyelinating tomaculous neuropathy. J Neurosci. 1997; 17(12): 4662-71. Epub 1997/06/15. PubMed PMID: 9169527.
33. Sancho S, Magyar J P, Aguzzi A, Suter U. Distal axonopathy in peripheral nerves of PMP22-mutant mice. Brain. 1999; 122 (Pt 8):1563-77. Epub 1999/08/04. PubMed PMID: 10430839.
34. Notterpek L, Ryan M C, Tobler A R, Shooter E M. PMP22 accumulation in aggresomes: implications for CMT1A pathology. Neurobiol Dis. 1999; 6(5):450-60. Epub 1999/10/21. doi: 10.1006/nbdi.1999.0274. PubMed PMID: 10527811.
35. Bryant D M, Stow J L. The ins and outs of E-cadherin trafficking. Trends Cell Biol. 2004; 14(8):427-34. Epub 2004/08/17. doi: 10.1016/j.tcb.2004.07.007. PubMed PMID: 15308209.
36. Chies R, Nobbio L, Edomi P, Schenone A, Schneider C, Brancolini C. Alterations in the Arf6-regulated plasma membrane endosomal recycling pathway in cells overexpressing the tetraspan protein Gas3/PMP22. J Cell Sci. 2003; 116(Pt 6):987-99. Epub 2003/02/14. PubMed PMID: 12584243.
37. Zhang X, Chow C Y, Sahenk Z, Shy M E, Meisler M R, Li J. Mutation of FIG. 4 causes a rapidly progressive, asymmetric neuronal degeneration. Brain. 2008; 131(Pt 8):1990-2001. Epub 2008/06/17. doi: 10.1093/brain/awn114. PubMed PMID: 18556664; PubMed Central PMCID: PMC2724900.
38. Patzig J, Kusch K, Fledrich R, Eichel M A, Luders K A, Mobius W, et al. Proteolipid protein modulates preservation of peripheral axons and premature death when myelin protein zero is lacking. Glia. 2016; 64(1):155-74. Epub 2015/09/24. doi: 10.1002/glia.22922. PubMed PMID: 26393339.
39. Cornblath D R, Sumner A J, Daube J, Gilliat R W, Brown W F, Parry G J, et al. Conduction block in clinical practice. Muscle Nerve. 1991; 14(9):869-71; discussion 7-8. Epub 1991/09/01. PubMed PMID: 1922183.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method of treating hereditary neuropathy with liability to pressure palsies (HNPP), comprising administering to a subject in need of treatment for HNPP a therapeutically effective amount of a PAK1 inhibitor that is PF-3758309.

2. The method of claim 1, wherein the administration is oral, topical, intramuscular injection, or intraperitoneal injection.

3. The method of claim 2, wherein the administration is by intraperitoneal (i.p.) injection.

4. The method of claim 1, wherein the PAK1 inhibitor is formulated in a composition suitable for injection.

5. The method of claim 1, wherein the PAK1 inhibitor is administered at a dose of about 0.2-3 mg/kg.

6. The method of claim 1, wherein the PAK1 inhibitor is administered at a dose of about 0.25-3 mg/kg.

7. The method of claim 1, wherein the PAK1 inhibitor is administered at a dose of about 0.03-3 mg/kg.

8. The method of claim 1, wherein the PAK1 inhibitor is provided in a composition further comprising a pharmaceutically acceptable carrier.

9. The method of claim 8, wherein the composition is formulated for injection.

10. The method of claim 8, wherein the composition is provided in a unit dose form.

11. The method of claim 1, and further comprising the step of monitoring the subject's symptoms that are associated with hereditary neuropathy with liability to pressure palsies.

12. The method of claim 11, wherein the symptoms being monitored are selected from the group consisting of numbness, loss of reflexes and uncoordinated movements, poorly controlled blood pressure, blurred vision, memory problems, loss of bladder and bowel control, fatigue, a sensation of pins and needles, tingling, loss of muscle function (palsy), and pain.

13. The method of claim 1, wherein the subject is a mammal.

14. The method of claim 1, wherein the PAK1 inhibitor is administered at a dose of about 0.03-1 mg/kg.

* * * * *